(12) United States Patent
Opie et al.

(10) Patent No.: US 10,485,968 B2
(45) Date of Patent: Nov. 26, 2019

(54) MEDICAL DEVICE FOR SENSING AND OR STIMULATING TISSUE

(71) Applicant: The University of Melbourne, Parkville (AU)

(72) Inventors: Nicholas Lachlan Opie, Parkville (AU); Thomas James Oxley, New York, NY (US); Gil Simon Rind, Parkville (AU); Stephen Michael Ronayne, Parkville (AU); Sam Emmanuel John, Parkville (AU); Clive N. May, Parkville (AU); David B. Grayden, Parkville (AU)

(73) Assignee: The University of Melbourne, Parkville (AU)

( * ) Notice: Subject to any disclaimer, the term of this patent is extended or adjusted under 35 U.S.C. 154(b) by 0 days.

(21) Appl. No.: 15/957,574

(22) Filed: Apr. 19, 2018

(65) Prior Publication Data

US 2018/0236221 A1 Aug. 23, 2018

Related U.S. Application Data

(63) Continuation of application No. PCT/US2016/057768, filed on Oct. 19, 2016.
(Continued)

(30) Foreign Application Priority Data

Oct. 20, 2015 (AU) ................................ 2015904302
Dec. 4, 2015 (AU) ................................ 2015905045

(51) Int. Cl.
*A61N 1/39* (2006.01)
*A61N 1/05* (2006.01)
(Continued)

(52) U.S. Cl.
CPC .......... *A61N 1/0531* (2013.01); *A61B 5/0478* (2013.01); *A61F 2/91* (2013.01);
(Continued)

(58) Field of Classification Search
USPC ........................................................ 607/116
See application file for complete search history.

(56) References Cited

U.S. PATENT DOCUMENTS

| 6,018,682 A | 1/2000 | Rise |
| 6,171,239 B1 | 1/2001 | Humphrey |

(Continued)

FOREIGN PATENT DOCUMENTS

| JP | 2009519807 | 5/2009 |
| JP | 2009527303 | 7/2009 |

(Continued)

OTHER PUBLICATIONS

Oxley, T. et al. "Minimally invasive endovascular stent-electrode array for high-fidelity, chronic recordings of cortical neural activity," *Nature Biotechnology*, 34(3):320-327, Feb. 8, 2016.

*Primary Examiner* — Nicole F Lavert
(74) *Attorney, Agent, or Firm* — Levine Bagade Han LLP

(57) ABSTRACT

Devices, methods and systems for transmitting signals through a device located in a blood vessel of an animal, for stimulating and/or sensing activity of media proximal to the device, wherein the media includes tissue and/or fluid.

24 Claims, 30 Drawing Sheets

Related U.S. Application Data

(60) Provisional application No. 62/379,625, filed on Aug. 25, 2016.

(51) Int. Cl.

| | | |
|---|---|---|
| *A61F 2/91* | (2013.01) | |
| *A61B 5/0478* | (2006.01) | |
| *A61F 2/92* | (2013.01) | |
| *A61B 18/00* | (2006.01) | |

(52) U.S. Cl.
CPC ...... *A61F 2/92* (2013.01); *A61B 2018/00214* (2013.01); *A61B 2018/00267* (2013.01); *A61F 2250/0001* (2013.01); *A61F 2250/0002* (2013.01); *A61N 1/0534* (2013.01); *A61N 1/0539* (2013.01)

(56) References Cited

U.S. PATENT DOCUMENTS

| | | |
|---|---|---|
| 6,537,310 B1 | 3/2003 | Palmaz et al. |
| 6,820,676 B2 | 11/2004 | Palmaz et al. |
| 7,190,998 B2 | 3/2007 | Shalev et al. |
| 7,647,097 B2 | 1/2010 | Flaherty et al. |
| 7,751,877 B2 | 7/2010 | Flaherty et al. |
| 7,881,780 B2 | 2/2011 | Flaherty |
| 7,901,368 B2 | 3/2011 | Flaherty et al. |
| 7,991,461 B2 | 8/2011 | Flaherty et al. |
| 8,060,194 B2 | 11/2011 | Flaherty |
| 8,095,209 B2 | 1/2012 | Flaherty |
| 8,386,050 B2 | 2/2013 | Donoghue et al. |
| 8,560,041 B2 | 10/2013 | Flaherty et al. |
| 8,812,096 B2 | 8/2014 | Flaherty et al. |
| 9,220,899 B2 | 12/2015 | Cattaneo et al. |
| 9,375,330 B2 | 6/2016 | Sims et al. |
| 2004/0249302 A1 | 12/2004 | Donoghue et al. |
| 2005/0113744 A1 | 5/2005 | Donoghue et al. |
| 2005/0137646 A1 | 6/2005 | Wallace et al. |
| 2005/0137647 A1 | 6/2005 | Wallace et al. |
| 2005/0143589 A1 | 6/2005 | Donoghue et al. |
| 2005/0203366 A1 | 9/2005 | Donoghue et al. |
| 2005/0251239 A1 | 11/2005 | Wallace et al. |
| 2005/0267597 A1 | 12/2005 | Flaherty et al. |
| 2005/0273890 A1 | 12/2005 | Flaherty et al. |
| 2006/0049957 A1 | 3/2006 | Surgenor et al. |
| 2006/0058627 A1 | 3/2006 | Flaherty et al. |
| 2006/0058854 A1 | 3/2006 | Abrams et al. |
| 2006/0089709 A1* | 4/2006 | Helmus ............... A61F 2/91 623/1.44 |
| 2006/0167564 A1 | 7/2006 | Flaherty et al. |
| 2006/0189901 A1 | 8/2006 | Flaherty et al. |
| 2006/0206167 A1 | 9/2006 | Flaherty et al. |
| 2006/0241356 A1 | 10/2006 | Flaherty |
| 2006/0253166 A1 | 11/2006 | Flaherty et al. |
| 2006/0259107 A1 | 11/2006 | Caparso et al. |
| 2007/0032738 A1 | 2/2007 | Flaherty et al. |
| 2007/0106143 A1 | 5/2007 | Flaherty |
| 2007/0142871 A1 | 6/2007 | Libbus et al. |
| 2007/0156126 A1 | 7/2007 | Flaherty |
| 2007/0239256 A1 | 10/2007 | Weber et al. |
| 2008/0009914 A1 | 1/2008 | Buysman et al. |
| 2008/0015459 A1 | 1/2008 | Llinas |
| 2008/0027346 A1 | 1/2008 | Litt et al. |
| 2008/0118546 A1 | 5/2008 | Thatcher et al. |
| 2008/0119911 A1 | 5/2008 | Rosero |
| 2008/0183253 A1 | 7/2008 | Bly |
| 2009/0131873 A1 | 5/2009 | Spear et al. |
| 2009/0221896 A1 | 9/2009 | Rickert et al. |
| 2010/0023021 A1 | 1/2010 | Flaherty |
| 2010/0063411 A1 | 3/2010 | Donoghue et al. |
| 2010/0106259 A1 | 4/2010 | Llinas et al. |
| 2010/0114195 A1 | 5/2010 | Burnes et al. |
| 2010/0152812 A1 | 6/2010 | Flaherty et al. |
| 2010/0292602 A1 | 11/2010 | Worrell et al. |
| 2013/0090651 A1 | 4/2013 | Smith |
| 2013/0206454 A1 | 8/2013 | Cattaneo et al. |
| 2013/0231658 A1 | 9/2013 | Wang et al. |
| 2013/0282084 A1* | 10/2013 | Mathur ............... A61N 5/00 607/101 |
| 2014/0058528 A1 | 2/2014 | Contreras-Vidal et al. |
| 2014/0142570 A1 | 5/2014 | Bakczewitz et al. |
| 2014/0180391 A1* | 6/2014 | Dagan ............... A61F 2/915 623/1.15 |
| 2014/0288667 A1 | 9/2014 | Oxley |
| 2015/0105772 A1 | 4/2015 | Hill et al. |
| 2015/0230742 A1 | 8/2015 | Silver |
| 2018/0303595 A1 | 10/2018 | Opie et al. |
| 2019/0046119 A1 | 2/2019 | Oxley |

FOREIGN PATENT DOCUMENTS

| | | |
|---|---|---|
| JP | 2010516384 | 5/2010 |
| JP | 2010516405 | 5/2010 |
| WO | WO 2003/101532 | 12/2003 |
| WO | WO 2005/001707 | 1/2005 |
| WO | WO 2005/046469 | 5/2005 |
| WO | WO 2005/051167 | 6/2005 |
| WO | WO 2005/051189 | 6/2005 |
| WO | WO 2005/065738 | 7/2005 |
| WO | WO 2005/092183 | 10/2005 |
| WO | WO 2005/107852 | 11/2005 |
| WO | WO 2006/015002 | 2/2006 |
| WO | WO 2006/020794 | 2/2006 |
| WO | WO 2006/041738 | 4/2006 |
| WO | WO 2006/073915 | 7/2006 |
| WO | WO 2006/074029 | 7/2006 |
| WO | WO 2006/076164 | 7/2006 |
| WO | WO 2006/076175 | 7/2006 |
| WO | WO 2006/078432 | 7/2006 |
| WO | WO 2006/086086 | 8/2006 |
| WO | WO 2006/105478 | 10/2006 |
| WO | WO 2007/058950 | 5/2007 |
| WO | WO 2007/078410 | 7/2007 |
| WO | WO 2007/146060 | 12/2007 |
| WO | WO 2008/019384 | 2/2008 |
| WO | WO 2008/094345 | 8/2008 |
| WO | WO 2008/094789 | 8/2008 |
| WO | WO 2009/135075 | 11/2009 |
| WO | WO 2010/078175 | 7/2010 |
| WO | WO 2013/049887 | 4/2013 |
| WO | WO 2017/070252 | 4/2017 |
| WO | WO 2018/195083 | 10/2018 |

* cited by examiner

MEDICAL DEVICE FOR SENSING AND OR STIMULATING TISSUE

RELATED APPLICATIONS

The present application is a continuation of PCT/US2016/057768 filed Oct. 19, 2016 now WO 2017/070252 which is a non-provisional application of Australian Provisional Application 2015904302 filed Oct. 20, 2015; Australian Provisional Application 20150905045 filed Dec. 4, 2015 and U.S. Provisional Application No. 62/379,625 filed Aug. 25, 2016, the entirety of each of which is incorporated by reference.

TECHNICAL FIELD OF THE INVENTION

The present invention relates to a medical device for implantation into a blood vessel of an animal.

BACKGROUND OF THE INVENTION

Any discussion of document, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and broad consistory statements herein.

In the United States alone, nearly two million people suffer from various neuromuscular disorders where control of limbs is severely impaired. In many of these patients, however, the portion of the brain responsible for movement remains intact, and it is disease and trauma to the spinal cord, nerves and muscles that limit mobility, function and independence. For these people, the ability to restore lost control at even a rudimentary level could lead to a greatly improved quality of life.

At present, there are two primary options for restoring function. One option is to increase the capabilities of the remaining pathways, substituting paralysed or amputated muscles with those under voluntary control. While this method has been highly successful for amputees by re-innervating forearm nerves into abdominal muscles which control a bionic arm, the restored function greatly depends on the site of damage or condition, with people paralysed by brainstem or high cervical injuries only able to achieve minor functional improvement. A second option is to provide the brain with a new communication and control channel to convey messages to the external world. Currently, these brain controlled interfaces (BCIs) measure electroencephalographic or other electrophysiological activity via surgically implanted epidural, subdural, and intracortical electrodes. While cortical measurements performed with electrodes placed on the scalp enable non-invasive neuronal measurements, they require daily application and are prone to noise and movement related artefacts. Penetrating and non-penetrating intracranial electrodes, implanted after a craniotomy directly onto the surface of a cortical area, have much better signal to noise ratios (relative to scalp electrodes) and have been shown to enable rudimentary prosthetic hand operation. These methods, however, require invasive surgery and carry a relatively high risk of complication, which can involve infections and bleeding. Furthermore, craniotomies are limited in access to the central nervous system, with many motor and sensory cortex areas hidden and inaccessible within cortical folds. These approaches are restricted in position and cannot be relocated once implanted and are subject to signal deterioration due to glial scar formation surrounding penetrating electrodes.

Thus, there remains a need to record and stimulate from cortical tissue in a method which is minimally invasive whilst also ensuring longevity and efficacy of recorded and induced signals.

By using blood vessels as a conduit to the brain, the risks associated with craniotomies, and the invasive creation of a burr hole in the skull of the patient is removed whilst also removing current noise and movement related artefacts observed with non-invasive scalp electrodes. Despite the minimally invasive benefits provided by these types of procedures, it is preferable that thrombus formation caused by the blockage of blood flow through a vessel is prevented. It is also preferable that the electrical energy delivered to the electrodes be as efficient as possible, which will reduce the burden placed on the electrical circuitry. Optimisation of wireless telemetry aimed to send power and data directly through the body to the implanted device, will enhance device functionality and negate the risk of infection caused through lead wires creating a direct passage between the vessel and the external environment. The ability to implant coils inside blood vessels will similarly reduce surgical risks associated with perforated vasculature.

Thus, there remains a need to provide improved intravascular electrodes, telemetry circuitry and implantation positions that are capable of more efficiently transmitting and receiving electrical energy between vessels and external circuitry, while minimizing the occlusion of blood flow.

It is generally desirable to overcome or ameliorate one or more of the above mentioned difficulties, or at least provide a useful alternative.

SUMMARY OF THE INVENTION

According to the present invention, there is provided a medical device for implantation into a blood vessel of an animal, including: (a) a stent movable between a collapsed condition of use for insertion into said vessel and an expanded condition of use for resiliently bearing against a wall of said vessel; (b) one or more electrodes coupled to the stent for stimulating and/or sensing activity of media proximal to the device, wherein the media includes tissue and/or fluid. The term stent is meant to include any support structure that maintains, carries, supports or incorporates the one or more electrodes within the tissue and/or fluid. The term stent can include conventionally designed medical stents, alternatively, the term stent can include any mechanical framework or scaffolding that positions electrode elements within a body lumen, such as a vessel, and facilitates electrical coupling of the electrode element(s) to a lead or other conductive structure. In certain variations, portions of the support structure itself can function as electrodes.

According to the present invention, there is also provided a method of recording of neural information or stimulation of neurons from the superior sagittal sinus or branching cortical veins of a patient using the above described device, including the steps of: (a) implanting the device in either the superior sagittal sinus or branching cortical veins; (b) receiving activity; and (c) generating data representing said activity; and (d) transmitting said data to a control unit.

According to the present invention, there is also provided a method of for stimulation and recording neural information or stimulation of neurons from the visual cortex of a patient using the above-described device, including the steps of: (a) implanting the device in a vessel in the visual cortex of the patient; and (b) recording neural information associated with the vessel or stimulating neurons in accordance with received stimulation data.

According to the present invention, there is also provided a system for controlling use of apparatus coupled to an animal or human, including: (a) the above-described device, said device being adapted for placement within a vessel of an animal or human to stimulate and/or sense the activity of media proximal to the device; (b) a control unit adapted for communication with the device; (c) apparatus coupleable to the animal or human, said apparatus adapted for in communication with the control unit, wherein the control unit is adapted to perform the steps of: (i) receiving data from the device representing activity of media proximal to the device; (ii) generating control signals for the apparatus; and (iii) sending said control signals to said apparatus.

According to the present invention, there is also provided a control unit for controlling operation of apparatus coupled to an animal or a human, said control unit being adapted to perform the steps of: (a) receiving data from the above-described device, said data representing activity of media proximal to a vessel within which the device is placed; (b) generating control signals for controlling operation of the apparatus; and (c) sending said control signals to the apparatus.

The present disclosure further includes a medical device for use within a tubular body having a lumen, the medical device comprising: a frame structure forming a plurality of struts, where the frame structure is moveable between a reduce profile and an expanded profile in which a diameter of the frame structure increases; where at least one of the plurality of struts forming the frame structure comprises an electrically conductive material on a support material, the electrically conductive material extending along at least a portion of the strut and being covered with a non-conductive material; at least one electrode formed by an opening in the non-conductive material on the portion of the strut; and a lead located at an end of the frame structure and configured to be in electrical communication with the electrically conductive portion, the lead extending from the frame structure.

The medical device can further include a connector block configuredto electrically couple the medical device to an external device, where the lead extends from the frame structure to the connector block.

In another variation, the present disclosure includes a method of recording of neural information or stimulation of neurons a patient the method comprising: receiving a signal representative of neural activity from a device positioned in a vessel of the patient; generating data representing said activity using the signal; and transmitting said data to a control unit; generating a control signal from the control unit; and transmitting the control signal to an apparatus coupled to the patient.

The present disclosure also includes a system for controlling an apparatus coupled to an animal or human. In one example, the system comprises a device adapted for placement within a vessel of the animal or human to stimulate and/or sense the activity of media proximal to the device; a control unit adapted for communication with the device, wherein the control unit is adapted to: (i) receive data from the device representing activity of media proximal to the device; (ii) generate a control signal; and (iii) transmit the control signal to said apparatus.

The system can include an apparatus selected from or more of the following: an exoskeleton; a prosthetic limb; a wheelchair; a computer; and/or an electrical or electro-mechanical device.

BRIEF DESCRIPTION OF THE DRAWINGS

Preferred embodiments of the present invention are hereafter described, by way of non-limiting example only, with reference to the accompanying drawing in which:

FIG. 5B is a cross-section view through the line A-A of the device shown in FIG. 5a;

DETAILED DESCRIPTION OF PREFERRED EMBODIMENTS OF THE INVENTION

Figure 1:
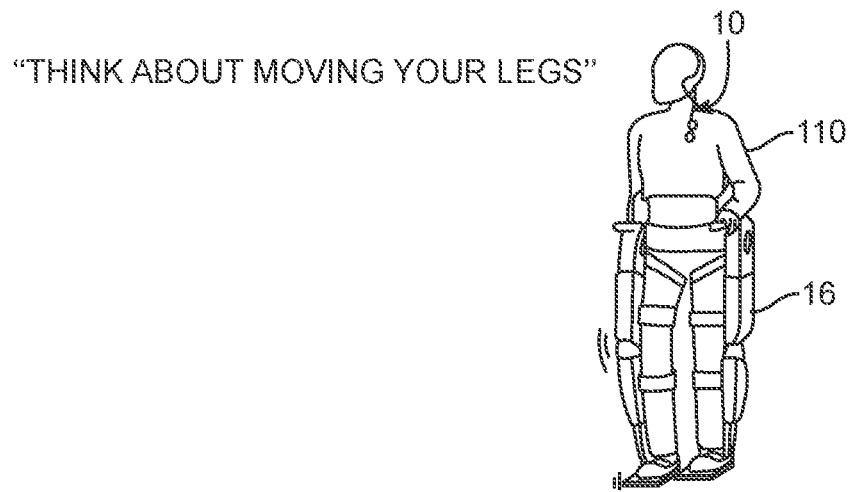
FIG. 1 is a diagrammatic illustration of a system for controlling use of apparatus coupled to an animal or a human.

The system 10 shown in FIGS. 1 to 4 includes: 1) a medical device 100 designed for placement within a vessel 103 of an animal or human 110 to stimulate and/or sense the activity of media (tissue and fluids) proximal (adjacent or touching) to the device 100, whether this be located inside or outside the vessel 103; 2) a control unit 12 (also referred to as a connector block and telemetry system) adapted for communication with the device; 3) a communication conduit 14 for facilitating communications between the device 100 and the control unit 12; and 4) apparatus 16 coupleable to the animal or human 110, the apparatus 16 adapted for communication with the control unit.

The control unit 12 can be adapted to perform the steps of: (a) receiving data from the device 100 representing activity of media proximal to the device 100; (b) generating control signals for the apparatus 16; and (c) sending the control signals to the apparatus 16. In some variations, the system includes connector block (illustrated by element 12) that functions as connector and acts as an extension of the communication conduit. In variations of the system, the control unit/connector block: is hermetically sealed and insulates the leads from the device to the control unit; can be inserted using zero-contact force attachments or attachments that do not require excessive force to insert (i.e., using balseal spring contacts); has a portion of the lead that is made from a stiffer silicone or similar material for handling and insertion into the connector. Variations of the device can include markers to identify portions of the leads that are stiffer (and can be handled) to distinguish from leads that cannot be handled. Such markers can include line-style markers, different colours or other indicators to clearly identify the regions. Variations of the connector block can have a fitting (e.g., clasp) such that multiple connectors can be inserted (i.e., two contact connectors (with 8 contacts each) for a 16 electrode Stentrode lead). The fitting can ensure securing of the contacts, alignment and prevention of water ingress When the medical device 100 is inserted adjacent to the motor cortex in the manner shown in FIGS. 2A, 2B, and 3, the system 10 can be used, for example, to control operation of an exoskeleton, and/or an artificial limb in the manner shown in FIG. 1.

This device 100 is implanted into blood vessels 103, from which, it will utilise electrodes mounted on a self-expanding member 101 to record or stimulate neighbouring tissue. Information is to be passed from or to the electrodes through the communication conduit 14, inside of the blood vessel 103, to a telemetry system 12 that, in turn, passes information (using wires or wirelessly) to or from an external apparatus 16, which includes (but is not limited to) one or more of the following:

(a) an exoskeleton; (b) wheelchair; (c) computer; and/or (d) other electrical or electro-mechanical device.

As such, in one specific application, the implanted medical device 100 has the capability to enable a paralysed patient 110 to use their thoughts directly to command and control a gait aid such as an exoskeleton or robotic legs 16.

Other applications for the implantable medical device 100 include (but are not limited to): (a) detection and prevention of seizures; (b) detection and prevention of involuntary muscular or neural control (for example to alleviate symptoms associated with: (i) multiple sclerosis; (ii) muscular dystrophy; (iii) cerebral palsy; (iv) paralysis and (v) Parkinsons'; (c) detection and therapeutic alleviation of neurological conditions, such as: (i) post-traumatic stress disorder; (ii) obsessive compulsive disorder; (iii) depression; and (iv) obesity; (d) direct brain control of computers and equipment, such as: (i) vehicles; (ii) wheelchairs; (iii) gait aids; robotic limbs; (e) direct input for sensory stimulation for: (i) blindness (connection to a camera); (ii) deafness (connection to microphone); (iiii) proprioception (connection to touch-sensitive robotic and computer systems); (f) internal assessment of personal health and wellbeing: (i) heart rate; (ii) respiration rate; (iii) temperature; (iv) environmental conditions; (v) blood sugar levels; and (vi) other biochemical and neurological markers; (g) internal communication (telepathy) between implanted groups of people utilising the device for information transmission, auditory, visual and proprioceptive feedback (for example, real time communication of what the implantee sees or hears); and (h) augmentation and optimisation of musculskeletal control and dexterity (for performance enhancement or rehabilitation).

Figure 2A:
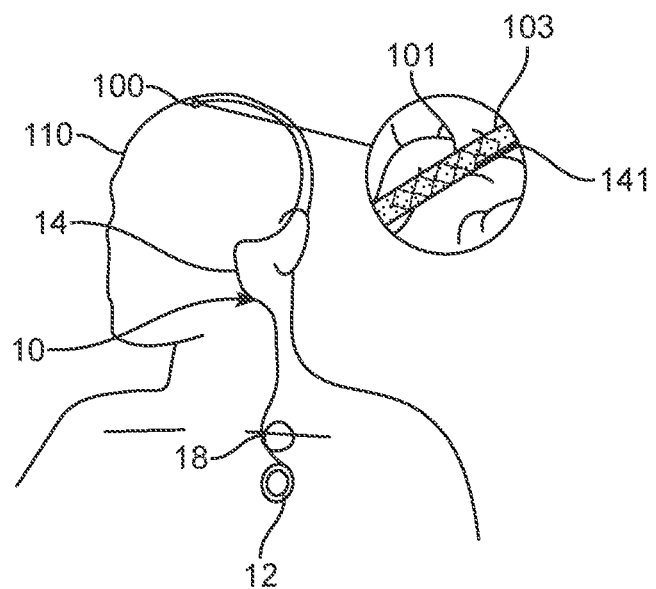
FIG. 2A is a diagrammatic illustration showing parts of the system shown in FIG. 1.
Figure 2B:
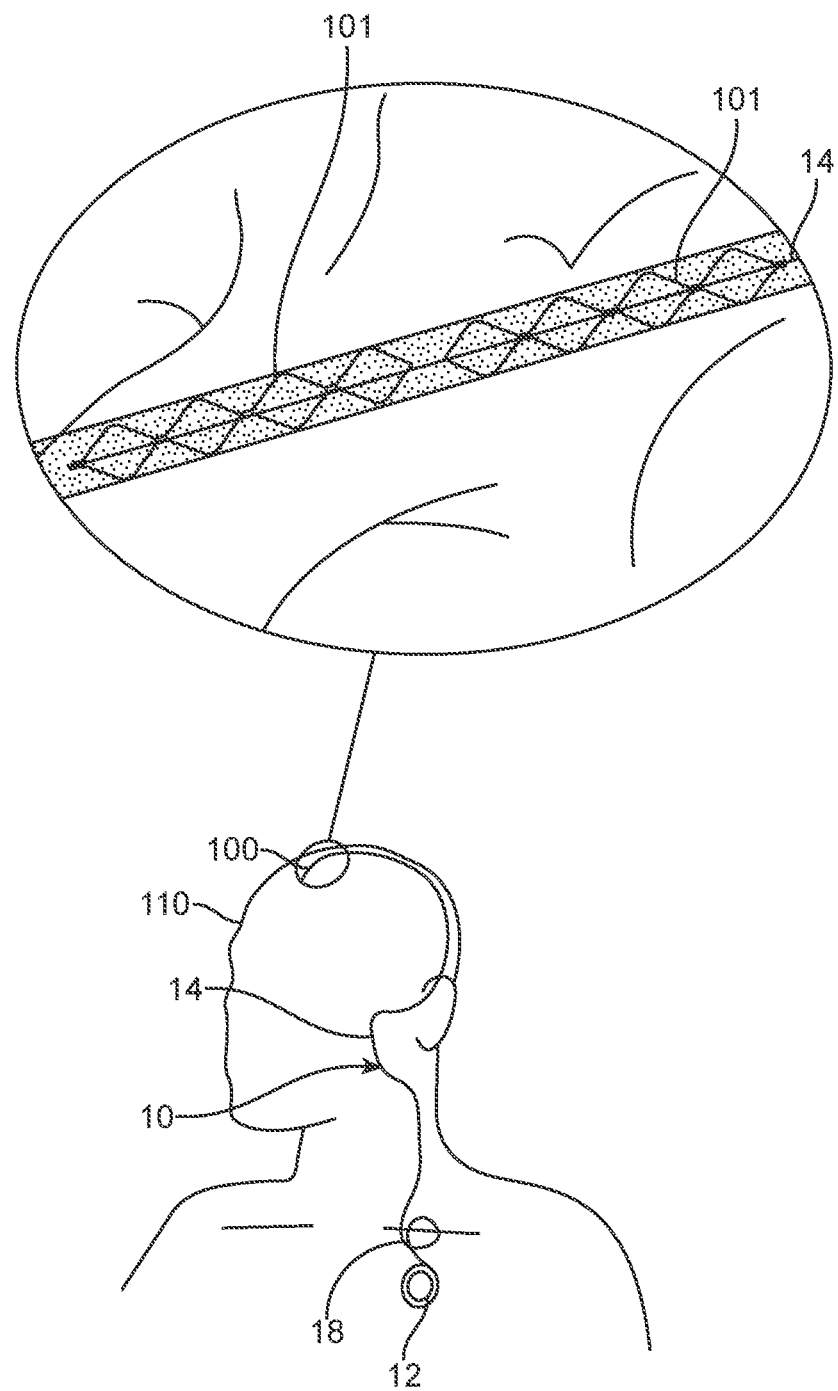
FIG. 2B is a diagrammatic illustration showing of an additional variation of the system comprising two or more stents.
Figure 3:
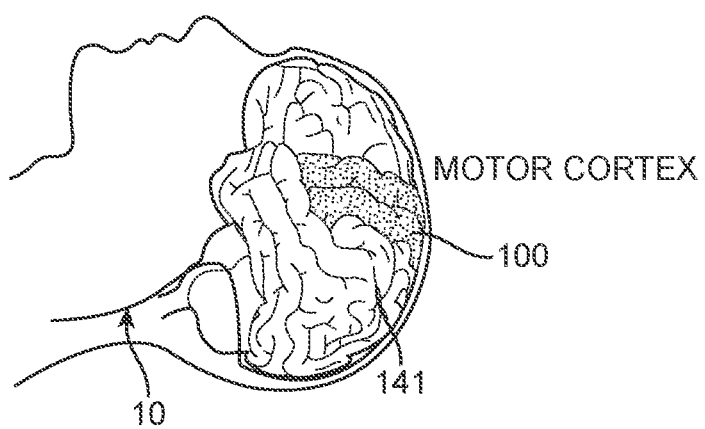
FIG. 3 a diagrammatic illustration showing parts of the system shown in FIG. 1.
Figure 4:
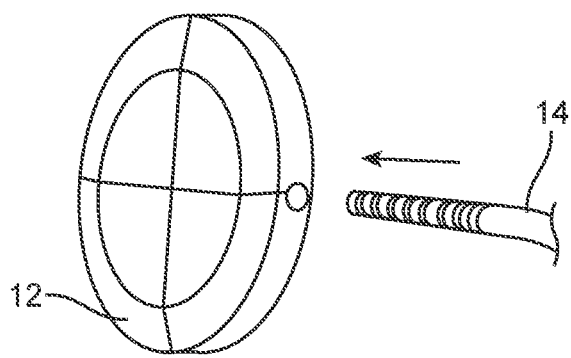
FIG. 4 is a diagrammatic illustration of a control unit of the system shown in FIG. 1.

FIG. 2B illustrates a two-stent 101 system. For purposes of illustration, the stents are positioned in a single vessel. However, the stents can be configured such that they can be positioned in separate vessels. The stents 101 can be joined by non-conductive material to form a power receiver and transmitting antenna. Alternatively, the stents can be coupled by one or more wires or conductive elements. Moreover, the system can include active electronics between the stents 101.

The devices described herein can be positioned in any number of areas of brain structures depending upon the desired outcome. For example, as discussed in Teplitzky, Benjamin A., et al. "Computational modeling of an endovascular approach to deep brain stimulation." *Journal of Neural Engineering* 11.2 (2014): 026011.stents can be positioned as follows: Internal capsule for depression and obsessive compulsive disorder (OCD); thalamus for epilepsy (E), Parkinsons' Disease, essential tremor, Tourette syndrome, consciousness disorder, chronic pain, obsessive compulsive behavior; fornix for Alzheimer's disease; globus pallidus internus for dystonia, depression, Tourette syndrome; hippocampus for epilepsy; hypothalamus for obesity, anorexia mentosa; inferior thalamic pduncle for depression and obsessive compulsive disorder; lateral habenula for depression, obesity, anorexia mentosa; nucleus accumbens for depression, obsessive compulsive disorder, addiction, obesity, anorexia mentosa; periaqueductal/periventricular for chronic pain; subgenal cingulate white matter for depression; subthalamic nucleus for Parkinson's Disease, dystonia, depression, obsessive compulsive disorder, epilepsy; and ventral capsule for obsessive compulsive disorder.

1. Medical Device

As shown in FIGS. 5a, 5b, 5d and 6, the medical device 100 generally includes: a. a collapsible and expandable stent 101; b. a plurality of electrodes 131 coupled to the stent 101; c. electrode lead wires 141 electrically coupled to electrodes 131; d. an olive 112 coupled to the stent 101 by an olive wire 114 for preventing perforation of vessels during implantation; e. implanted chips; f. contacts 151 couple to the lead wires 141 to enable communication between the device 100 to the control unit 12; and g. a stent shaft 121 is used to deploy the device 100.

Electrode lead wires 141 can be electrically connected to at least one electrode and will be wound around the stent strut lattice 108 such that mechanical compression and extension is not interfered with. Electrode wires 141 may be wound around the stent shaft 121, thread through a stylet shaft or may form part of the stent shaft directly. Lead wires 141 will form connections with electrode contacts 151 on the opposite end of the stent shaft to the stent, whereby electrical contact a connector block mechanism 12 enables the connection path with external equipment 16, which included but is not limited to computers, wheelchairs, exoskeletons, robotic prosthesis, cameras, vehicles and other electrical stimulation, diagnostic and measurement hardware and software.

The term electrode 131 is used in this specification to refer to any electrical conductor used to make contact with media in and/or around a blood vessel 103.

A detailed description of the operation of each of these components is set out below.

The Stent

The stent 101 includes a plurality of struts 108 coupled together with strut cross links 109.

Figure 7A:
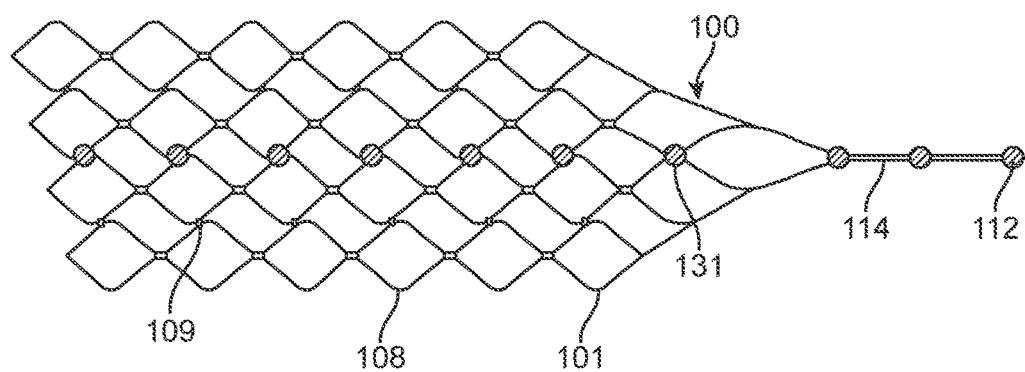
FIGS. 7A to 7E are diagrammatic illustrations of medical device of the system shown in FIG. 1.

In the arrangement shown in FIG. 7a, the device 100 includes nine electrodes coupled to the stent 101 in a linear pattern. As shown, the stent 101 appears flat. The top of the stent 101 may be directly joined to the bottom of the stent 101 or will curve around to meet (without permanent attachment) the bottom of the stent 101.

Figure 7B:
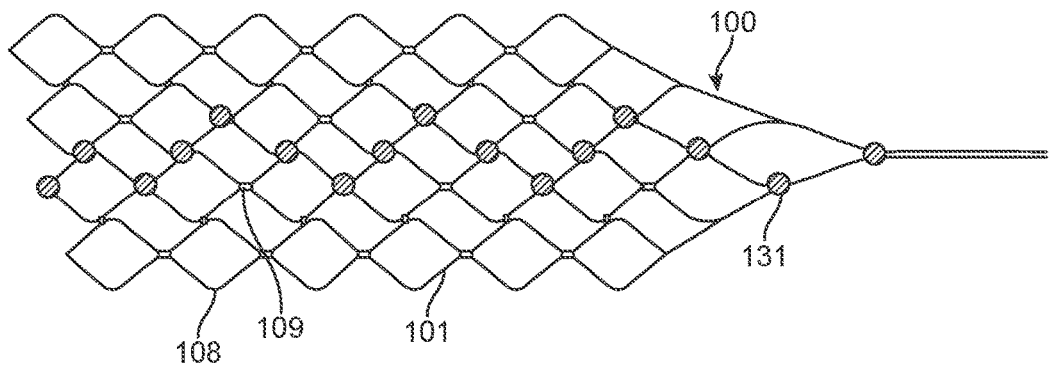
Figure 7C:
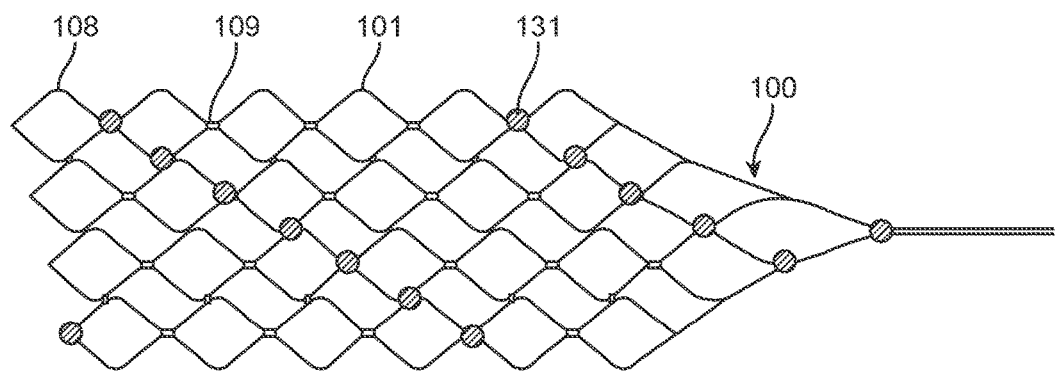
Figure 7D:
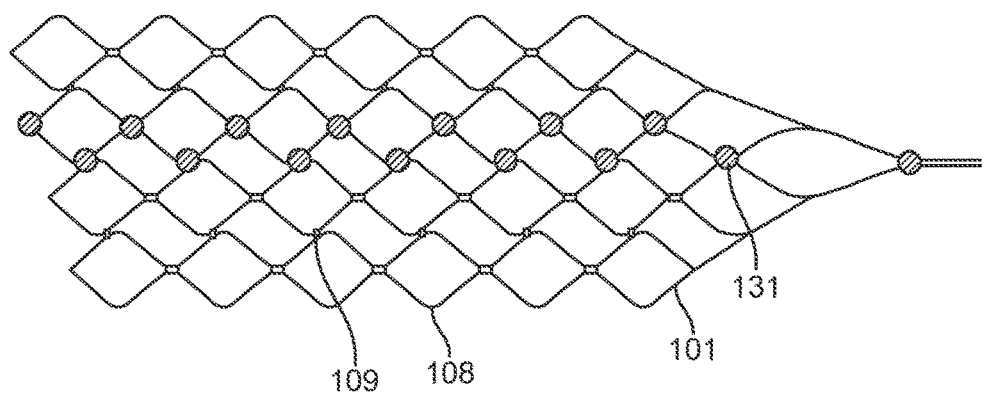
Figure 7E:
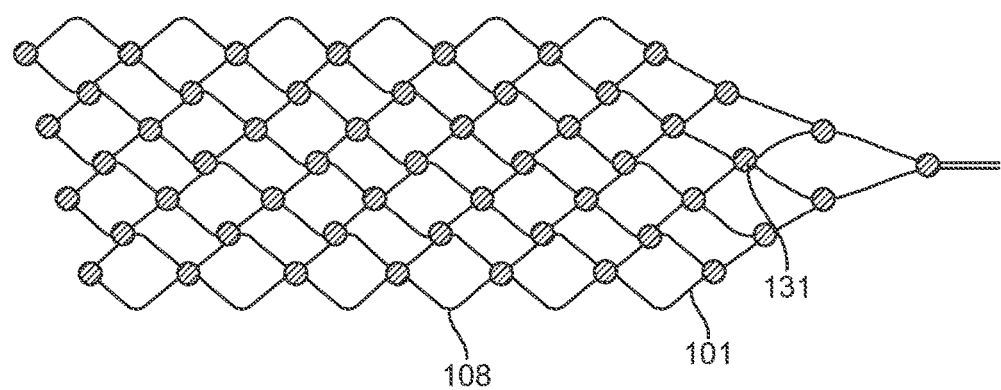
Figure 8A:
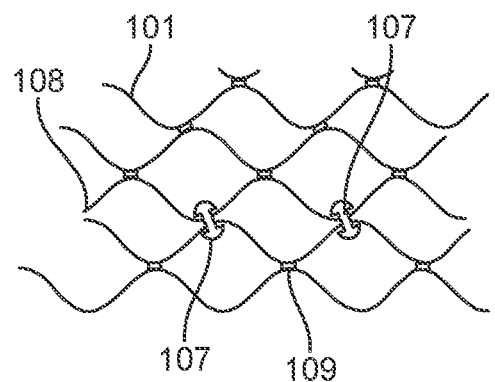
FIG. 8A is a diagrammatic illustration showing electrode mounting platforms of a medical device of the system shown in FIG. 1.
Figure 8B:
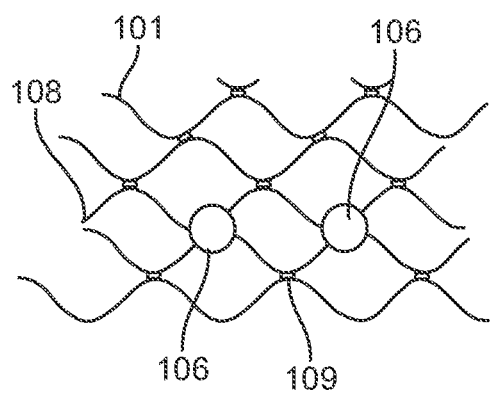
FIG. 8B is a diagrammatic illustration showing placements of a medical device of the system shown in FIG. 1.

Alternatively, the device 100 includes a stent with any suitable number of electrodes 131 arranged in any suitable configuration. For example, the electrodes can be configured as follows: the sinusoidal arrangement of electrodes 131 shown in FIG. 7b; the spiral arrangement of electrodes 131 shown in FIG. 7c to enable 360 degree contact of an electrode to the vessel wall once deployed; the reduced amplitude sinusoidal arrangement of electrodes 131 shown in FIG. 7d for increased coverage whilst still ensuring only one stent is at each vertical segment; and the dense arrangement of electrodes shown in FIG. 7e for increased coverage. The stent 101 is laser cut or woven in a manner such that there is additional material or markers where the electrodes 131 are to be placed to assist with attachment of electrodes and uniformity of electrode locations. For example, if a stent 101 was fabricated by laser cutting material away from a cylindrical tube (original form of stent), and, for example, electrodes are to be located at 5 mm intervals on the one axis, then electrode mounting platforms 107, 108 can be created by not cutting these areas from the tube. Similarly, if the stent is made by wire wrapping, then additional material 107, 108 can be welded or attached to the stent wires providing a platform on which to attach the electrodes. Alternatively, stents can be manufactured using thin-film technology, whereby material (Nitinol and or platinum and or other materials or combinations of) is deposited in specific locations to grow or build a stent structure and/or electrode array Electrodes As particularly shown in FIG. 8a, the device 100 includes electrode placements 107 coupled to strut cross links 109. The placements 107 are used to coupled the electrodes 131 to the stent. An alternative embodiment of the placements 106 is shown in FIG. 8b. In this embodiment, the placements are circular.

As shown, the electrodes 131 are located on or at the stent cross links 109. Locating the electrodes in these positions allows for changes in shape of the stent 101 (i.e expanding and collapsing) without significantly affecting the integrity of the electrodes. Alternatively, may also be located in between the stent strut crosslinks (not depicted).

Figure 9:
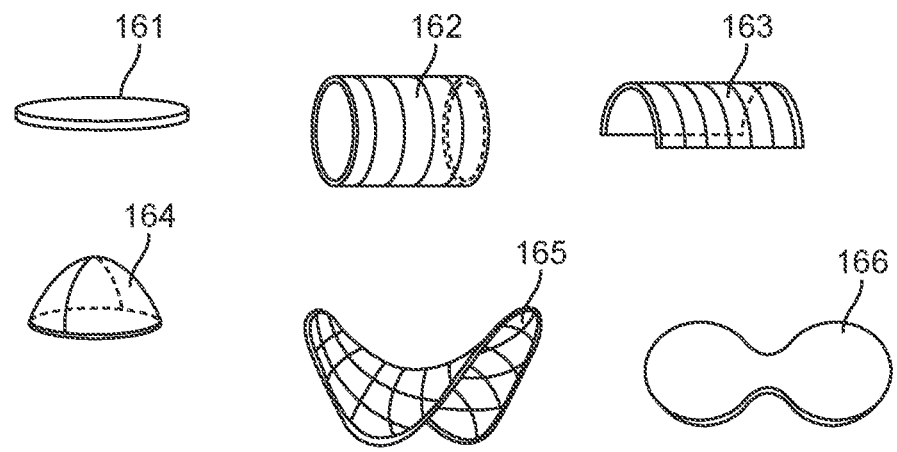
FIG. 9 shows diagrammatic illustrations of different electrode configurations.

FIG. 9 depicts different electrode geometries which include but are not limited to: flat discs 161; cylinders or rings 162; half-cylinders or rings 163; spheres, domes or hemispheres 164; hyperbolic parabaloids 165; and double electrodes or electrodes whereby they are preferentially longer along one axis 166.

Figure 10:
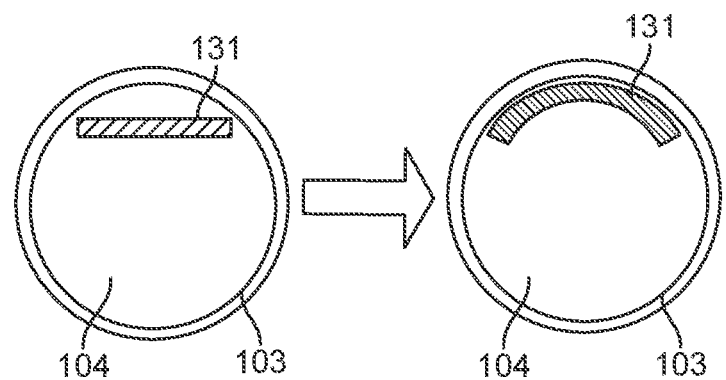
FIG. 10 shows diagrammatic illustrations of different electrode configurations.

As shown in FIG. 10, the electrodes 131 preferably include shape memory material and hence the electrodes 131 may be uninsulated sections of the device 100. As shown, the electrode 131 inside a patient and the vessel 104 is unobstructed. After activation of shape memory, the electrode 131 conforms to better fit the vessel wall 103.

To enhance contact and functionality of the device 100, electrodes 131 include the attachment of additional material (shape memory alloy or other conducting material) through soldering, welding, chemical deposition and other attachment methods to the stent 101 including but not limited to: directly on or between the stent struts 108; to lead wires 14 passing from the electrodes 131 to wireless telemetry links or circuitry; and directly to an olive 112 placed on the distal aspect of the device 100 to or stent shafts.

To further enhance the device 100 performance, there may be one or more electrodes 131 per wire strand 141 and there may be one or more strands 141 utilised per device 100. These strands 141 may be grouped to form a bundle 144, which may be woven in alternate sinusoidal paths around the stent struts 108 in the manner shown in FIG. 11. Similarly, there may be one or more wires 141 designated to each electrode 131 and hence there may be one or more electrodes 131 per device 100. Thus, multiple electrodes 131 may be used simultaneously.

To optimise the ability of the electrodes 131 to stimulate or record from medium (including but not limited to neural tissue, vascular tissue, blood, bone, muscle, cerebrospinal fluid), the electrodes 131 may be positioned at pre-determined intervals based on the diameter of the target vessel 103 to allow each of the electrodes 131 to be in contact with the vessel 103 in the same orientation (ie, all electrodes facing to and in contact with the left vessel wall upon deposition). Electrodes 131 may be mounted such that recordings or stimulation can be directed to all 360 degrees of the vessel simultaneously. Similarly, to enhance the recording and stimulation parameters of the electrodes 131, the electrode sizes may be varied, with larger electrodes 131 used to assess greater areas of neighbouring medium with smaller electrodes 131 utilised for localisation specificity.

Alternatively, the electrodes 131 are made from electrically conductive material and attached to one or more stents, which form the device 100 and allow for multiple positions. In this embodiment, the electrodes 131 are made from common electrically active materials such as platinum, platinum-iridium, nickel-cobalt alloys, or gold, and may be attached by soldering, welding, chemical deposition and other attachment methods to one or more lead wires 141, which may be directly attached to the shape memory shaft(s). The electrodes 131 are preferably one or more exposed sections on the insulated lead wire 141 and the electrode lead wires may be wrapped around one or more shape memory backbones. There may be one or more electrodes and lead wires wrapped around a single shape memory backbone, and, where multiple shape memory backbones are used in the one device, the backbones may have different initial insertion and secondary deposition positions. Thus, they may be used for targeting multiple vessels simultaneously.

Figure 12:
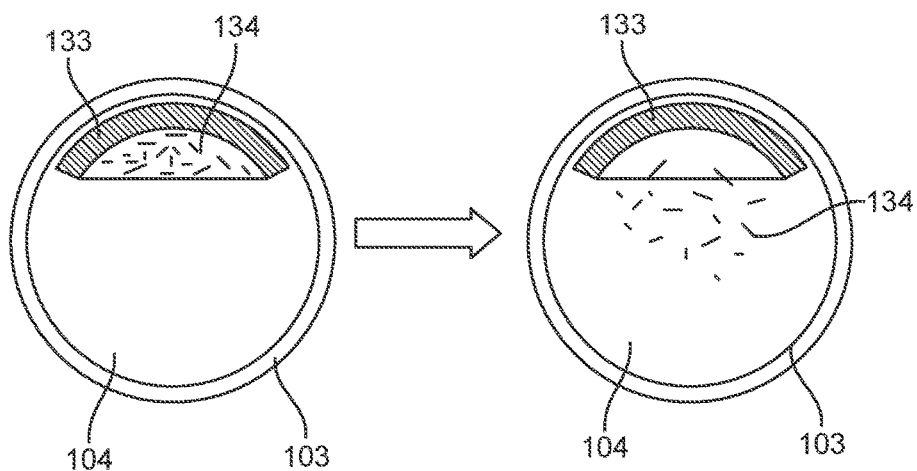
FIG. 12 shows diagrammatic illustrations of different electrode configurations.

As shown in FIG. 12, the electrodes 131 can be designed such that they are carriers of substances 134 and solutions such as therapeutic drugs, including but not limited to anti-thrombogenic, and materials. In this embodiment, the electrodes 131 are designed to release the drugs, either passively through diffusion or through control by an implanted electrical clock or manually through electrical stimulation of the electrodes 131. In this embodiment, the electrodes 131 are made from materials that have portions of the electrodes 131 that are not electrically conductive.

The drug 134 is preferably released into the vessel 104 upon timed, natural, electrical or otherwise activation, or into the vessel wall 103.

Electrode Wires

Figure 13A:
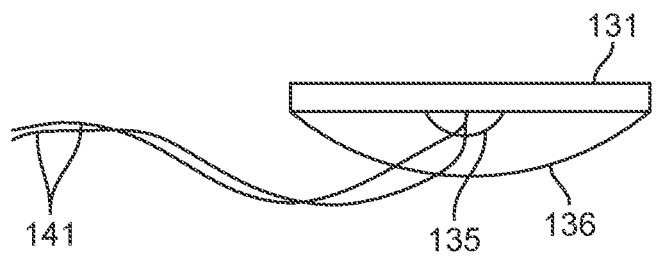
FIG. 13a is a diagrammatic illustration showing wire attachments to an electrode.

The electrode wires 141 are electrically coupled to respective electrodes in the manner shown in FIG. 13a. As shown, the electrical attachment 135 and the back face of the electrode is covered in a non-conductive substance 136.

The lead wires 141 are preferably wrapped around the stent 101 and along a shaft 121.

Figure 5A:
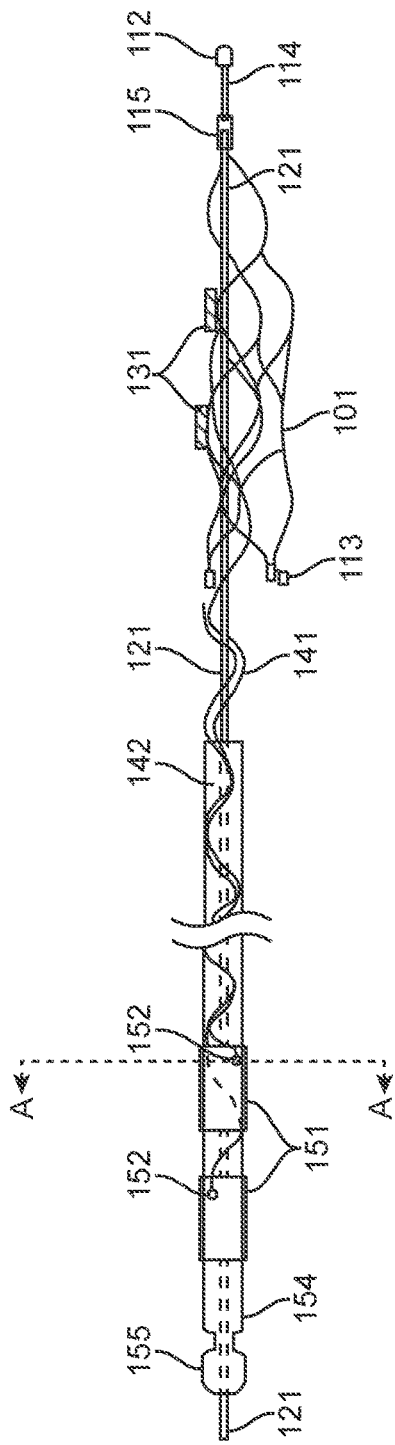
FIG. 5A is a diagrammatic illustration of a medical device of the system shown in FIG. 1.
Figure 5B:
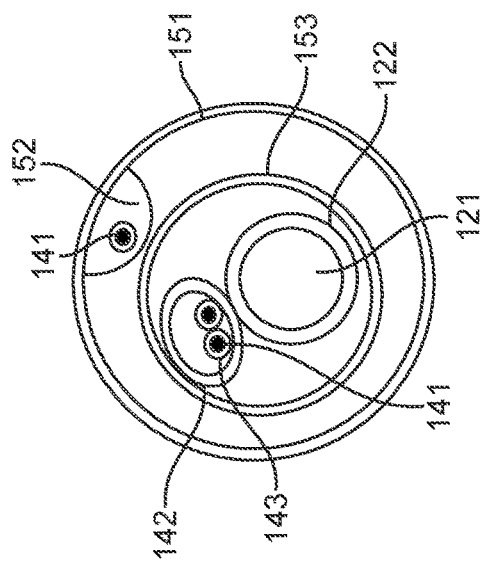
Figure 13B:
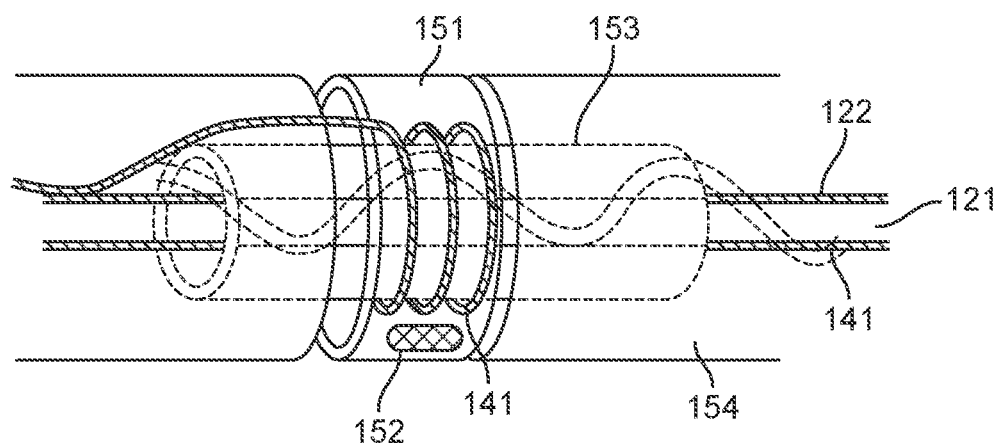
FIG. 13b is a diagrammatic illustration showing electrode lead wires wrapped around a shaft and covered in insulation forming a wire bundle or cable.

As shown in FIGS. 5a, 5b and 13b, the electrode lead wires 141 are wrapped around the shaft 121 and covered in insulation 122 forming a wire bundle or cable. A sleeve 153 wraps around the wire bundle at the location of the contact 151, whereby at least one wire 141 is wrapped around the sleeve 153 and connected to the contact 151 at a connection weld point 152. The over-molding 154 ensures a uniform diameter is present between contacts.

The sleeve 153 covers the wire bundle 142 with an exposed section of wire 141 attached 152 to a contact 151.

Distal electrodes and/or markers and/or buffers are also depicted 112 attached via a wire 114 to the stent 101. The shaft 121 is attached at the end of the stent at the attachment/detachment zone 115 and is shown passing through the sleeve 142 and electrode contacts 151 to exit behind past the connector securement point 155.

The lead wires 141 shown to be inside the sleeve 142 where they are wrapped around the shaft 121 where they make electrical contact at a contact weld 152 to the electrode contacts 151. An overcoat 154 is shown to ensure uniform diameter of the device between the contacts. The shaft 121 may be detached at the detachment zone 115 and removed following deployment in a vessel.

As shown in FIG. 13b, lead wires 141 are connected to electrode contacts 151. Electrode lead wires 141 are initially wrapped around a shaft 121 covered in insulation 122 forming a wire bundle or cable. A sleeve 153 is placed around the wire bundle at the location of the contact, whereby at least one wire 141 is wrapped around the sleeve and connected to the contact 151 at a connection weld point 152. Over-molding 154 may be used to ensure a uniform diameter is present between contacts.

As particularly shown in FIG. 5b, the stent shaft 121 is coated in an insulative layer 122, has a plurality of wires 141 that are insulated 143 and grouped in an insulated bundle 142 wrapped around it. A sleeve 153 covers the wire bundle 142 with an exposed section of wire 141 attached 152 to a contact 141.

The wires 141 are made from electrically conductive materials including but not limited to Platinum, Platinum/Tungsten, Stainless Steel, Nitinol, Platinum/Iridium, Nickel-Cobalt Alloys, or other conductive and biocompatible materials.

The wires 141 are between 10 um and 100 um thick (diameter), stranded cable or monofilament, and connect the electrodes 131 to the contacts 151. Alternatively, the wires 141 connect the electrode 131 to wireless circuitry retained on the stent or shaft.

Figure 11:
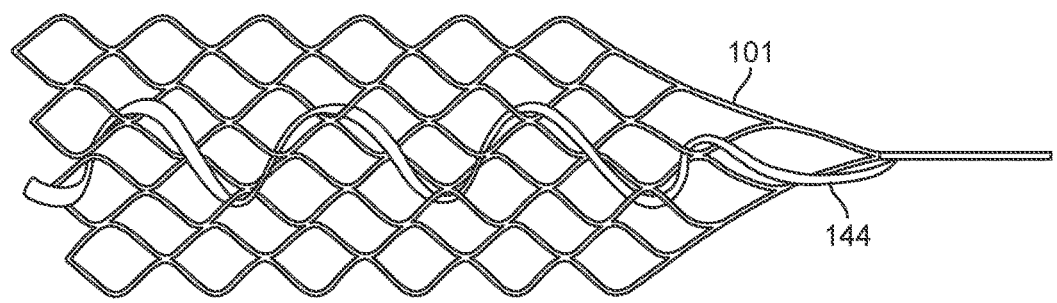
FIG. 11 is a diagrammatic illustration of a medical device of the system shown in FIG. 1.

The wires 141 are insulated with non-conductive material (ie, Teflon or polyimide). The wires 141 are wrapped around the stent struts in a sinusoidal pattern as shown in FIG. 11. Alternatively, the wires 141 are wrapped in a helical tube or wire bundle or cable, with the wire or bundle between 300 um and 2 mm in diameter (thickness)

The wires 141 are connected to contacts 151 using wire wrapping, conductive epoxy, welding, or other electrically conductive adhesion or connection means.

Olive

In the embodiment shown in FIG. 5a, the device 100 includes an olive 112 mounted at the distal tip to reduce risk of perforation and to improve device 100 safety during the implantation and deposition phase. In this arrangement, the olive 112 is directly connected to the front of the device 100 and act as a buffer, which is the first aspect of the device that comes in contact with the deployment catheter or the vessel during deployment. The olive 112 can additionally be used as a radiopaque distal marker. The olive 112 can be configured and attached to the stent 101 in many different forms including, but not limited to, the following:

i. Flexible Cord

As shown in FIG. 5a, the olive 112 is placed at a distance from the front of the stent 101, connecting with the stent 101 via a flexible cord 114.

ii. Spring Olive

Figure 14:
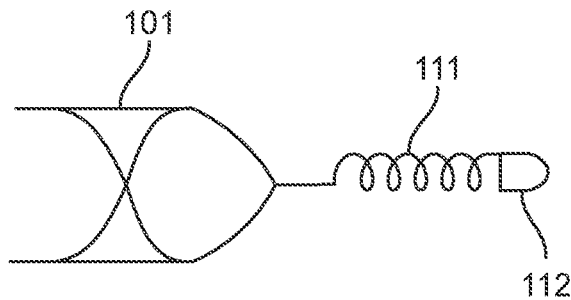
FIGS. 14 to 20 are diagrammatic illustrations showing different embodiments of the stent.

FIG. 14 depicts an olive placed on the distal end of a stent 101 whereby the olive is comprised of a buffer which may or may not be electrically active and function as an electrode 112 connected to the stent 101 by a flexible spring or helically wound wire 111.

iii. Multiple Olives

Figure 15:
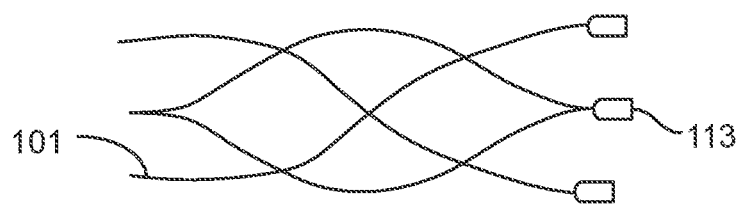

FIG. 15 depicts a plurality of olives placed on the distal end of a stent 101 whereby the olive is comprised of a plurality of buffers which may or may not be electrically active and function as an electrode 113.

iv. Short Olive

Figure 16:
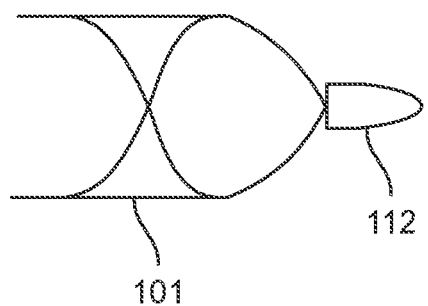

FIG. 16 depicts an olive placed on the distal end of a stent 101 whereby the olive is connected directly to the end of the stent which may or may not be electrically active and function as an electrode 112.

v. Shaped Wire Olive

Figure 17:
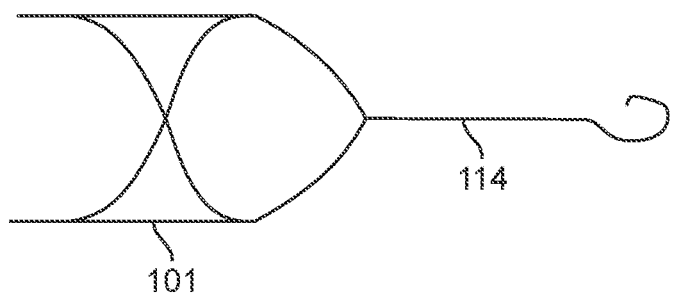

FIG. 17 depicts an olive placed on the distal end of a stent 101 whereby the olive is a flexible wire which may or may not be electrically active and function as an electrode and may or may not be shaped as a shepherds crook 114.

vi. Wire Olive

Figure 18:
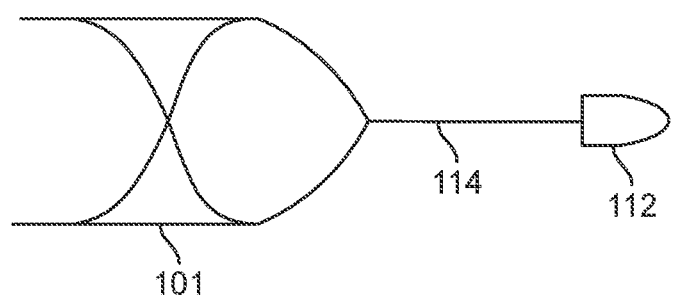

FIG. 18 depicts an olive placed on the distal end of a stent 101 whereby the olive is comprised of a buffer which may or may not be electrically active and function as an electrode 112 connected to the stent 101 by a flexible wire 114.

vii. Olive with Detachment Zone

Figure 19:
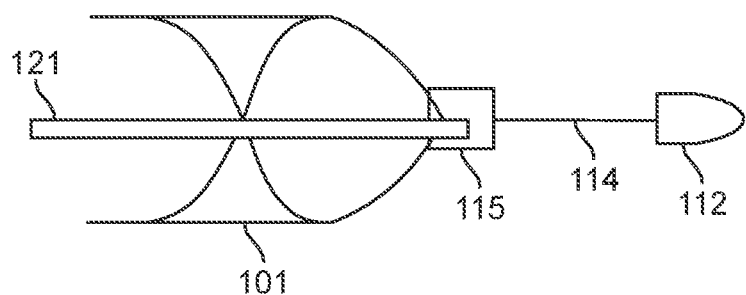

FIG. 19 depicts an olive placed on the distal end of a stent 101 whereby the olive is comprised of a buffer which may or may not be electrically active and function as an electrode 112 connected to the stent 101 by a flexible wire 114. This figure further depicts a shaft 121 that is connected to the stent 101 via an attachment and/or detachment zone 115.

Figure 20:
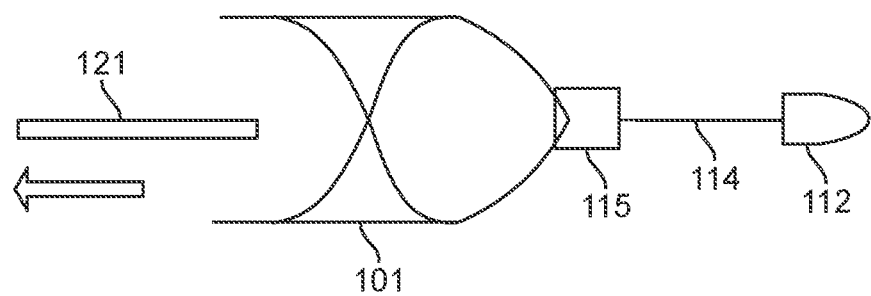

FIG. 20 further depicts the shaft 121 that is detached from the stent 101 via the attachment and/or detachment zone 115.

The flexible wire 114 includes but is not limited to electrically conductive and electrically insulating wires, springs, helical leads and tubes which may have a buffer at the front. Alternatively, the buffer is electrically conductive and acts as an electrode, comprising all the features of stent-mounted electrodes.

Implanted Chips

Implanted electrical circuitry (chips) are preferably used to control the stimulation and measurement of the electrodes 131. The chip can be implanted in place of an electrode (or elsewhere mounted on the stent), where the chip has the capacity to transmit the signals. The chip includes circuitry for: (a) signal amplification; (b) signal multiplexing; and (c) transmission of power and data.

The electrodes 131 are attached to one or more electrical chips (whereby the chip is defined as the electrical circuitry as well as the substrate which the chip is built on). Miniaturised chips are mounted on the stent 101 in a similar manner and position to the electrodes 131.

Alternatively, these chips may be attached at a distance from the neural recording or stimulation site such as the neck or pectoral region, or the chip may connect directly to external hardware, such as current sources, recording equipment or prostheses.

The chips preferably include circuitry for stimulation of neural tissue (current and/or voltage sources, batteries and/or capacitors or charge/energy storing components and switch matrices, etc) and circuitry for the recording of neural activity (amplifiers, power sources, switch matrices, etc) and blood composition (such as pH meters, salts and saline composition, glucose etc).

Further, chips may have circuitry required for the transmission of power and data through telemetry coils and self-monitoring hardware such as thermal sensors.

Figure 5C:
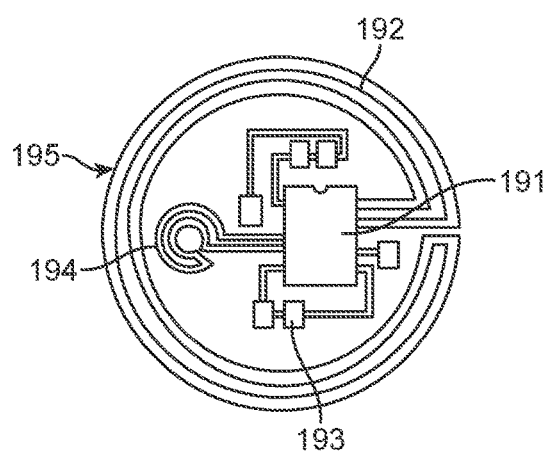
FIG. 5C is a schematic diagram of a wireless chip.
Figure 5D:
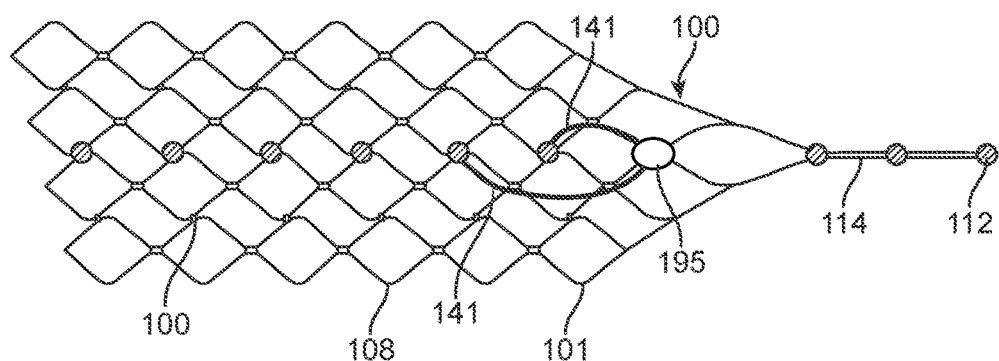
FIG. 5D is a diagrammatic illustration of a medical device of the system shown in FIG. 1.

The depiction of the wireless chip 195 shown in FIG. 5c, whereby the microprocessor 191 is shown as well as other components 193 (eg, capacitors, multiplexors, clocks, wireless transmitters, receivers etc). This depiction has two coils that can be used for transmission and receiving of both power and data, shown as a large coil 192 and a small coil 194.

The chip itself may contain a telemetry coil for the transmitting and receiving power and data and may contain a magnet to enable alignment with adjacent chips and telemetry coils or may be attached to shape memory alloys or other materials in which the telemetry coils are comprised.

The chip is preferably flexible, and may be pre-curved to the diameter of the vessel to allow for the deposition of the chip within a vessel. Thus, the chip may contain shape memory alloys or polymers to conform the chip to the curvature of the vessel during the deposition phase. The chip may also be mounted on a bioabsorbable or biodegradable substrate to allow for integration within a vessel. Multiple chips may be used simultaneously.

f. Contacts

As particularly shown in FIGS. 5a and 5b, electrode contacts 151 are required to enable connection of the device 100 to external equipment in the situation where wireless circuitry is not employed. The electrode contacts 151 are preferably made from materials similar to those used by the electrodes and will be of similar diameters. The contacts 151 are electrically insulated from each other and will be connected to the electrode lead wires 141 by (but not limited to) conductive epoxy, laser or resistance welding, soldering, crimping and/or wire wrapping.

The contacts 151 are platinum rings or rings of other conductive, biocompatible materials. The contacts can be made from or contain magnetic materials (ie, Neodinium).

The contacts 151 are preferably: (a) between 500 um and 2 mm in diameter; (b) between 500 um and 5 mm in length; and (c) between 10 um and 100 um in thickness.

The contacts 151 are shaped as discs, tubes, parabaloids or other shapes similar to those used for the electrodes 131.

The contacts are placed over non-conducting sleeve (including but not limited to a silicone tube, heat shrink, polymer coating) to assist with electrical insulation of other lead wires and electrode and stent wire, and to assist in retaining shape tubular shape whilst allowing some flexibility.

Preferably, the contacts 151 have a contact to contact separation of between 100 um and 10 mm.

The contacts 151 are formed through wire wrapping of the wires 141.

Preferably, at least one contact 151 is a dummy connector (including but not limited to a metal ring, magnetic ring, plastic tube). A dummy connector in this instance is a connector that is not in electrical contact with an electrode, instead, the purpose is to enable a connection or securing point (ie, through a screw terminal) to the device in a desired location and such that the contacts (connected to electrodes) are not damaged.

The contacts 151 are separated by a non-conductive sleeve (including but not limited to a silicone tube, heat shrink, polymer coating) to reduce electrical noise and prevent contact between superficial lead wires 141.

g. Shaft

Figure 21A:
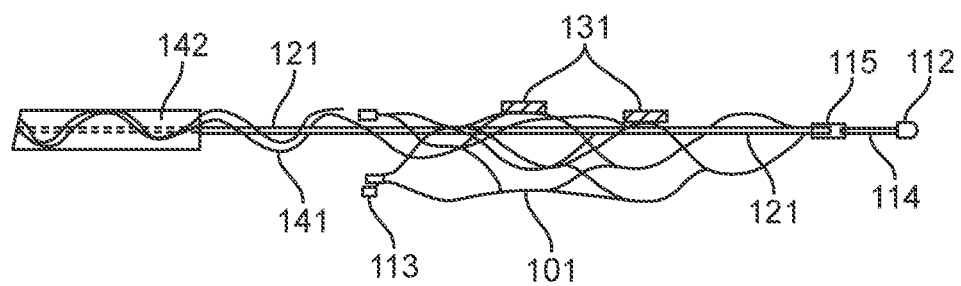
FIGS. 21a to 21c are diagrammatic illustrations showing deployment of different embodiments of the device.

As shown in FIG. 21a, to enable deployment, a flexible shaft 121 is connected to the device 100. In the example shown in FIG. 21a, the shaft 121 is connected at the distal end of the device 100 such that it acts to pull the device 100 from the front.

Figure 21B:
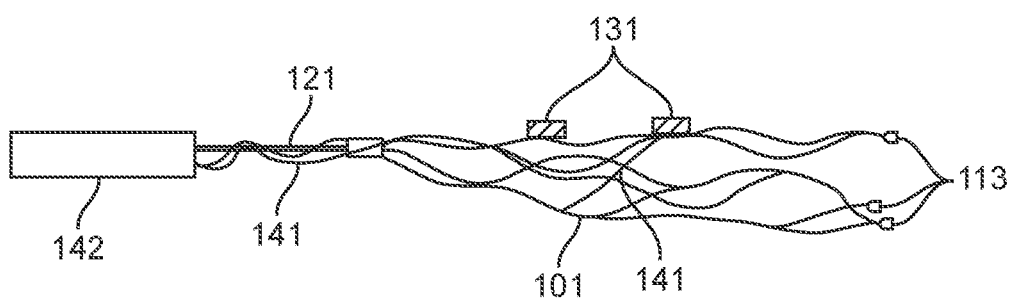

In the alternate embodiment shown in FIG. 21b, the shaft 121 is attached to the proximal end of the device 100 such that the shaft 121 pushes the device 100 from the back of the stent 101. In this embodiment, medical device 100 includes a plurality of electrodes 131 mounted to a stent 101 with electrode lead wires 141 wrapped around the stent 101 and the shaft 121 and covered in a sleeve 142. Distal electrodes and/or markers and/or buffers are also depicted 113 as is the stent detachment zone 105.

Figure 21C:
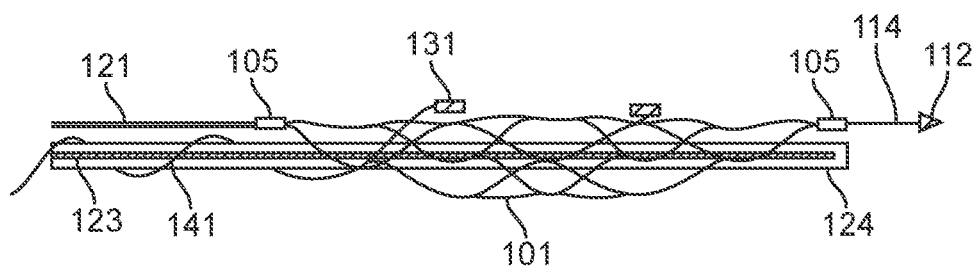

The further embodiment shown in FIG. 21c includes a double tapered stent 101 with mounted electrodes 131 and a stent shaft 121 attached to the stent 101 at the stent attachment/detachment zone 105. Another attachment/detachment zone 115 at the front of the stent 101 connects the stent 101 to the olive wire 114 and a stylet sleeve 124, through which, a removable stylet 123 is placed. Electrode wires 141 are shown as wrapped around the outside of the stylet sleeve 123 or as being fed through the centre.

There may be a plurality of wires, with both pushing and pulling abilities. The stent shafts 121 may be implanted permanently or may be designed to be detached and removed. In this embodiment, the attachment/detachment zone will be located at the junction of the stent shaft 121 and the stent 101. Detachment methods include, but are not limited to, electrochemical detachment, mechanical detachment and thermo-electrical detachment.

The stent shaft 121 can be used as a backbone for electrode lead wires 141, assisting the stability of the electrode lead wires 141 as they traverse from the electrodes 131 to the electrode contacts. In this embodiment, the electrode wires 141 are in a polymer 142, (including but not limited to shrink wrap, heat shrink, parylene, silicone, Teflon, etc) to provide additional mechanical support, assist in water retention and to enable coatings to be deposited onto the stent shaft where wires are present.

The stent shaft 121 may be a stylet that is removed following implantation and deposition of the device 100. In this embodiment, the stent shaft 121 may be a cylindrical tube such that the stylet 123 can be fed through the centre of the tube 121.

The wires 141 are preferably thread through the middle of a stylet sleeve.

Preferably, the wires 141 are wrapped around the stent shaft or stylet sleeve.

In a further embodiment, the electrode wires 141 that connect the electrodes 131 to the contacts 152 are wrapped in a wire bundle 144 and wrapped around an internal lumen tubing 145 in a helical form such that there is an internal lumen 147 whereby a removable stylet 148 can be thread during insertion and removed following deployment. This embodiment enabled removability of the stylet 148 and flexibility of the wire bundle 144 that is over coated in an external tubing 146.

Figure 21D:
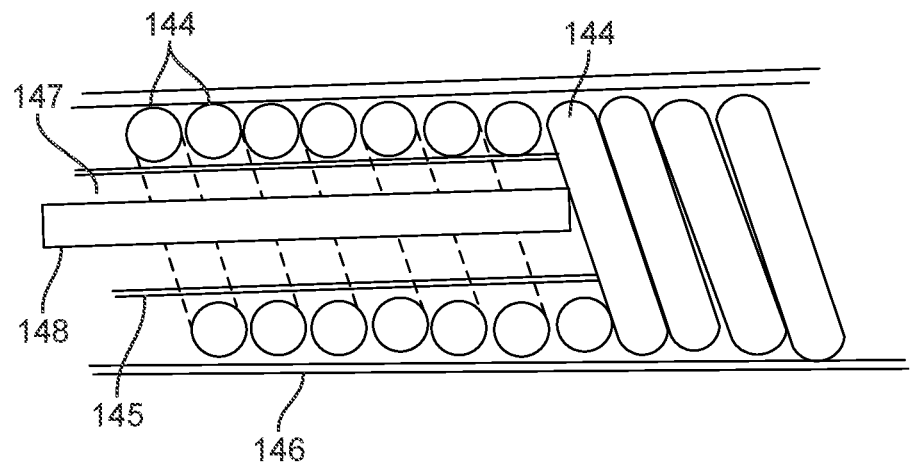
FIGS. 21d and 21e show additional information regarding a helical lead 114.
Figure 21E:
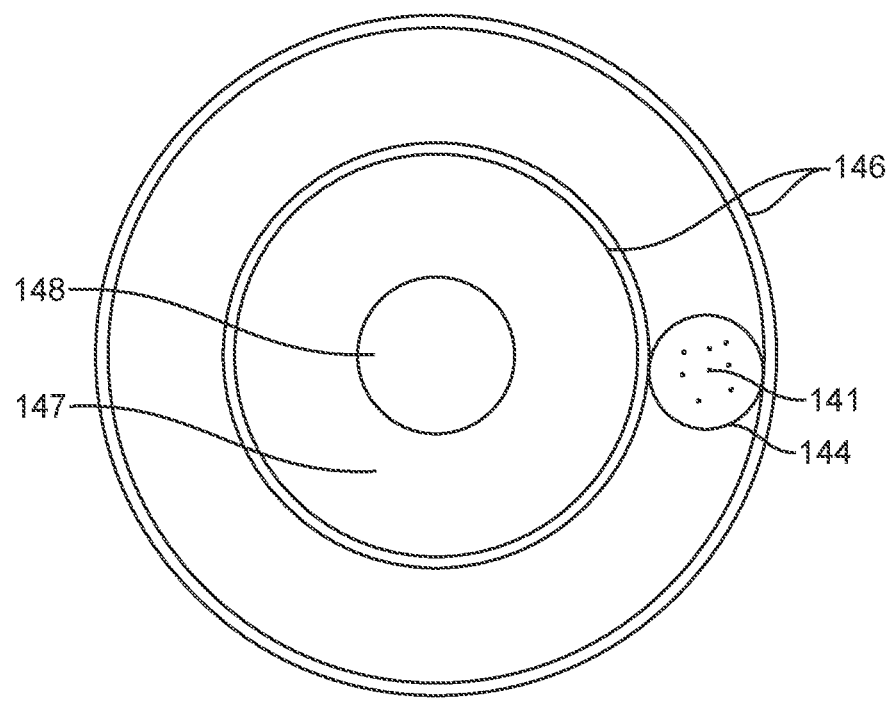

FIGS. 21d and 21e show additional information regarding a helical lead 114. As depicted, the helical 114 lead includes wire bundle 144 wrapped around an internal lumen tube 145. Through the internal lumen 147, a removable stylet 148 can be thread during delivery and removed following device placement Control Unit The control unit 12 shown in FIG. 2 is a wireless controller, relaying information and power through the skin wirelessly.

Figure 22:
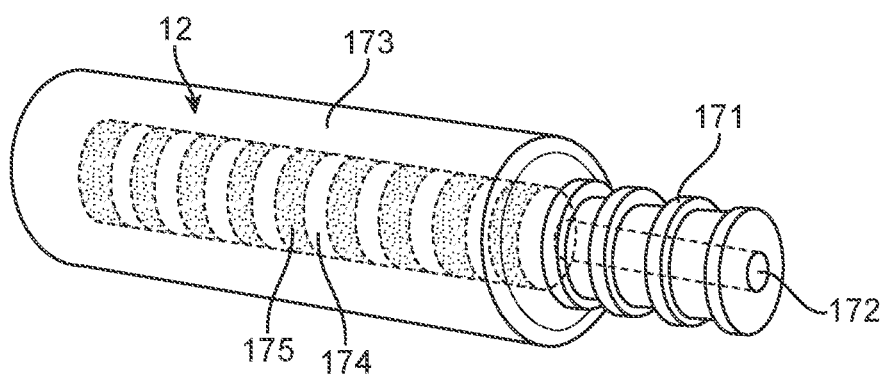
FIGS. 22 to 24 are diagrammatic illustrations of a control unit of the system shown in FIG. 1.
Figure 23:
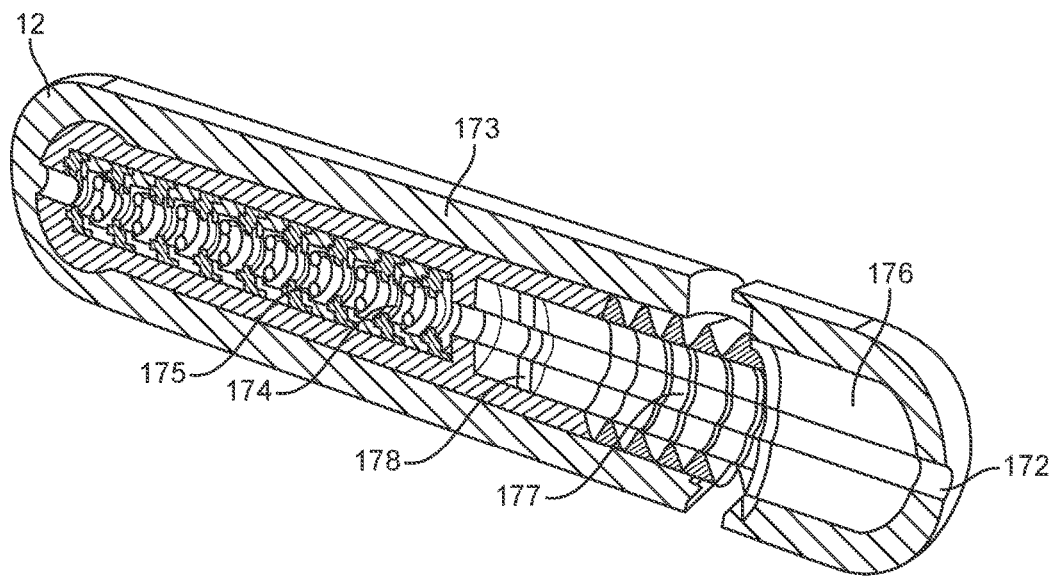
Figure 24:
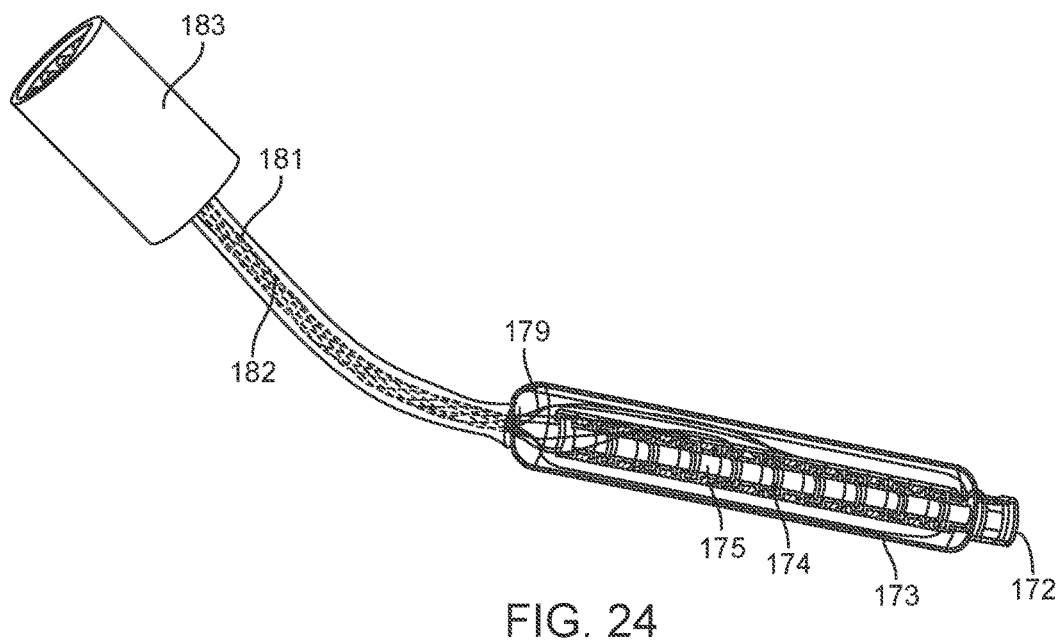

The connector block 12 in FIGS. 22, 23, and 24 are passive devices (ie, no circuitry). Essentially, it functions as an intermediate connection between the device 100 and external equipment. The device 100 is inserted into the connector block 12 whereby the device 100 contacts make electrical contact with internal contacts contained within the connector block 12. These internal contacts of the connector block 12 then form a thicker wire bundle which passes through the skin (the rest of the connector block is implanted) and can be connected to external equipment.

Essentially, as we are limited in space (the entire device must pass through a catheter as the catheter needs to be removed over the device after implantation) the connector block enables attachment of larger items to the thin device 100.

The embodiments shown in FIGS. 22, 23 and 24 are the same, although only FIG. 24 shows the wire that goes through the skin.

The control unit 12 shown in FIG. 22 is shaped to receive and make electrical connection with the lead 14. The control unit include contacts rings mounted on the inside. Here, the connector block 12 is secured and ensured water-tight through attachment of silicone and/or sutures at the grooved end.

The wireless system that is implanted on the stent directly is essentially the same (although a miniaturised version) of the wireless system 12 in FIG. 2.

As shown in FIG. 23, the electrode lead 14 is inserted and a silicone gasket is used to make a watertight seal following FIG. 24 depicts a connector block whereby the electrode lead 14 is thread through the connection opening 172 whereby the contacts connect with the electrically conductive connectors 175 inside the connector block body 173. Separation and electrical insulation and water-tightness is increased through silicone (or otherwise) separators 174. Contacts 175 are welded (or otherwise) to connector block wires 179 that may form a silicone or otherwise 181 encased bundle 181 to terminate at a wireless or direct electrical connection port 183.

Method of Using the System

Figure 25:
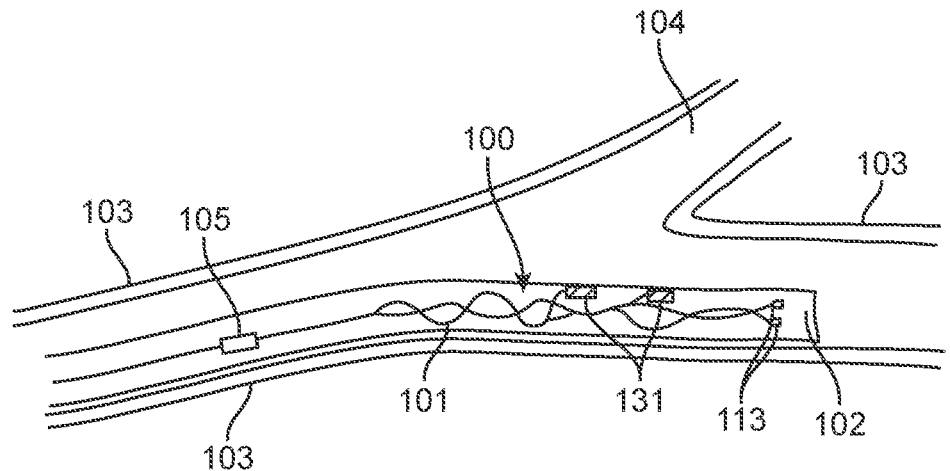
FIGS. 25 and 26 are diagrammatic illustrations showing different stages of deployment of the device.
Figure 26:
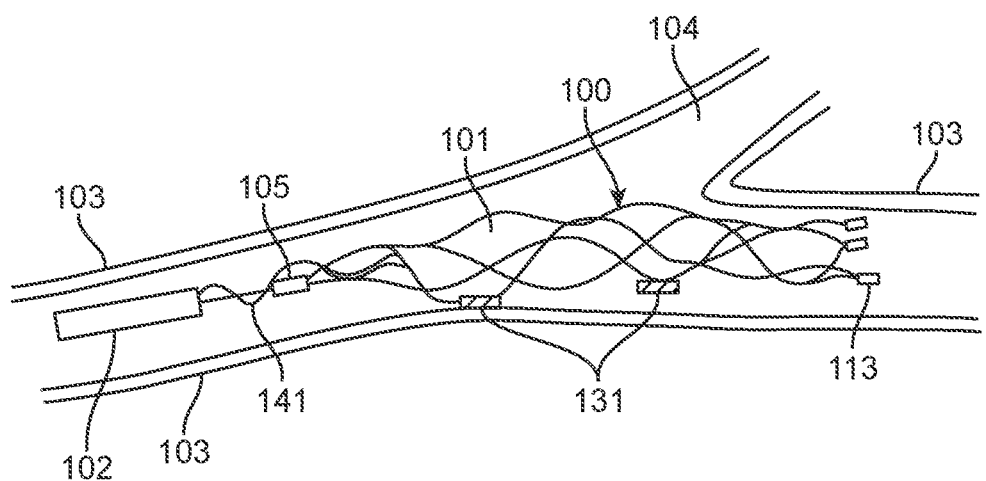

The device 100 is movable between an insertion position shown in FIG. 25 and the deposition or scaffolding position shown in FIG. 26.

In the insertion position, the device 100 is contracted and thus thin enough to be threaded through the vasculature pathway from within a catheter from an entry point (ie, the jugular vein) to a deposition point (eg, the motor cortex).

When arranged in the deposition or scaffolding position, the device 100 is in an expanded condition where scaffold electrodes mounted on the outside of the stent 101 as pressed against the vessel wall. This expanded position anchors the device 100 in its location within the vessel 103. Further, this deposition position is designed such that it has a minimal effect on blood flow integrity through the vessel 103 in which the device 100 is deposited. The scaffolding position may be synonymous to a spring, coil or helical strand, whereby the device 100 is in contact with the vessel wall only, reducing the effect on blood flow. Electrodes 131 may also be mounted on the inside of the stent 101 such that information from fluid flowing through the expanded stent 101 can be measured. For a stent 101 to be removed or relocated, additional shafts (other than that used for initial deployment) are required. These are explained in the context of this invention, with both single tapered and double tapered designs used.

To enable the device 100 to be arranged in multiple positions, the material used is such that multiple states are possible. These materials include, but are not limited to, Nitinol and other shape memory alloys and polymers. Further, to enhance the long term biocompatibility of the device 100, the polymers may be bioabsorbable or biodegradable, with a time of degradation similar to the time in which fibrosis occurs over the device 100. Hence, the electrodes 131 (which preferably are not designed to degrade, and may be made from Nitinol, shape memory alloys, conductive polymers, other non-shape memory alloys and inert and biocompatible metals such as platinum, iridium, stainless steel and gold) will be all that remains of the initial device 100 and will become embed inside the blood vessel 103, further enhancing the stability of the device 100 at the location of deposition Device in Blood Vessel (after Deployment)

Figure 6:
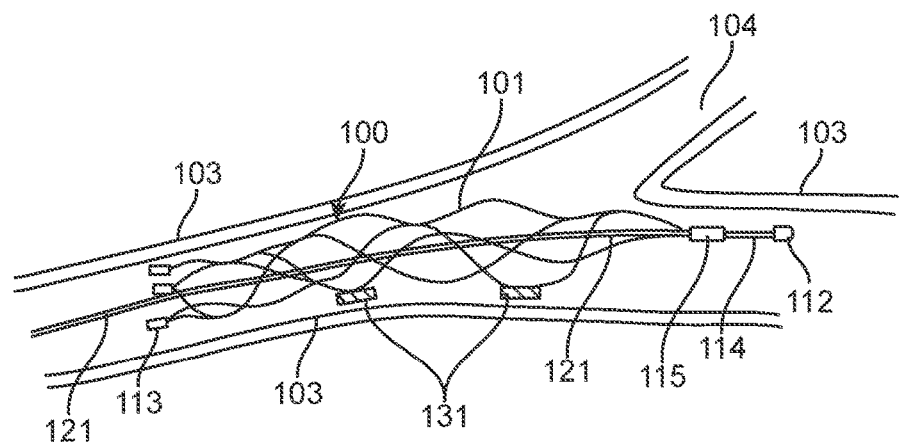
FIG. 6 is a diagrammatic illustration of a medical device located in a vessel.

FIG. 6 depicts a medical device 100 in the expanded or deposition or scaffolding position. The device 100 includes a stent 101, distal olives and/or proximity markers 112, a wire 114 attaching the stent 101 to the olive 112, a plurality of electrodes 131, and an attachment/detachment zone 115 whereby the shaft is connected to the stent 101 having been deployed in a blood vessel 104. Stent 101 mounted electrodes 131 are in direct apposition with the vessel wall 131 and are depicted as not interruptive of blood flow to any vessel (both the vessel the device is deployed in and other connected vessels). Here, the olive 112 can be used to direct the medical device into the desired vessel 104.

Device in Blood Vessel Pre-Deployment

FIG. 25 depicts a medical device 100 during implantation (surgical deployment phase) as it is being thread through vessels 104 inside a catheter 102. The stent 101, electrodes 131, stent detachment zone 105 and stent distal markers/electrodes/buffers 113 are shown, as are the vessel walls 103. Here, the catheter 102 is being used to select and direct the device into the desired vessel 104.

Device in Blood Vessel after Deployment

FIG. 26 depicts a medical device 100 in the expanded or deposition or scaffolding position comprising a stent 101, distal olives and/or proximity markers 113, a plurality of electrodes 131, lead wires 141 and a stent detachment zone 105 being deployed in a blood vessel 104 through a deposition catheter 102. Stent 101 mounted electrodes 131 are in direct apposition with the vessel wall 103 and are depicted as not interruptive of blood flow to any vessel (both the vessel the device is deployed in and other connected vessels).

Ground Electrode

Figure 27:
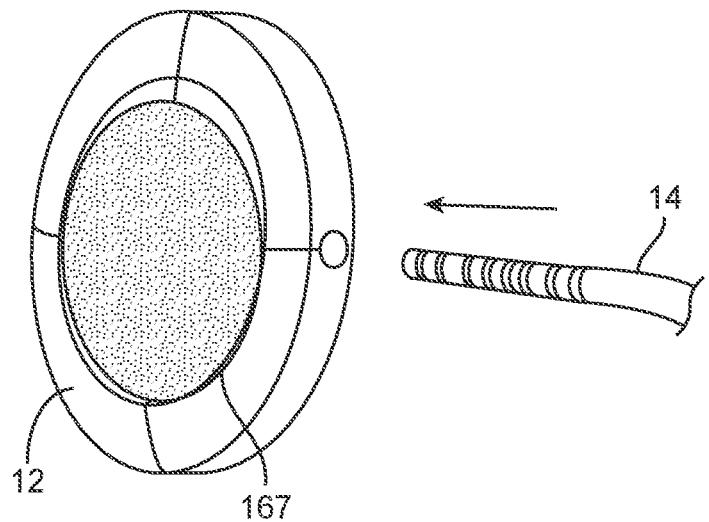
FIGS. 27 and 28 are diagrammatic illustrations of control units having ground electrodes attached thereto.

The system preferably includes a ground electrode 167, configured in the manner shown in FIG. 27, which is used to assist and improve the quality of the recorded signals or to provide an electrical return path for stimulation applications. Here the ground electrode may be placed on the connector block provided it is implanted. Ground electrode 167 is preferably directly attached to the outside of the wireless controller 12.

Figure 28:
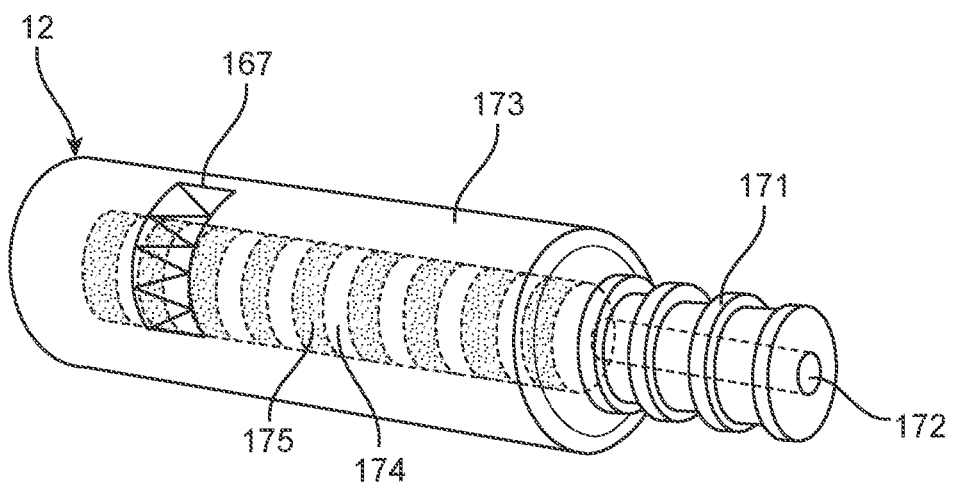

An alternative embodiment of the ground electrode 167 is shown in FIG. 28. Ground electrode 167 on the outside of the controller 12.

Figure 37:
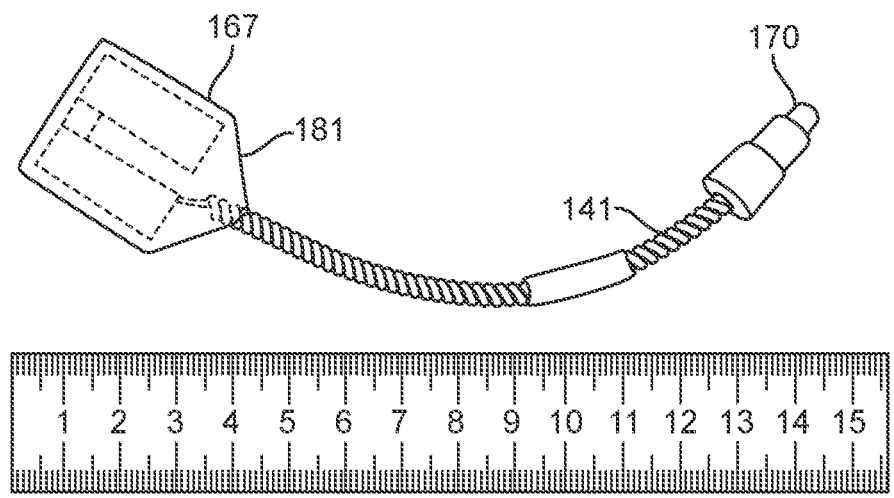
FIG. 37 is a photo of a C-shaped ground electrode.

The platinum C-shaped ground electrode 167 shown in FIG. 37 is embed in silicone 181 with a red helical lead wire 141 that is attached to a standard electrical terminal 169. Dacron mesh is used to assist secure the electrode and wire to tissue.

Figure 29:
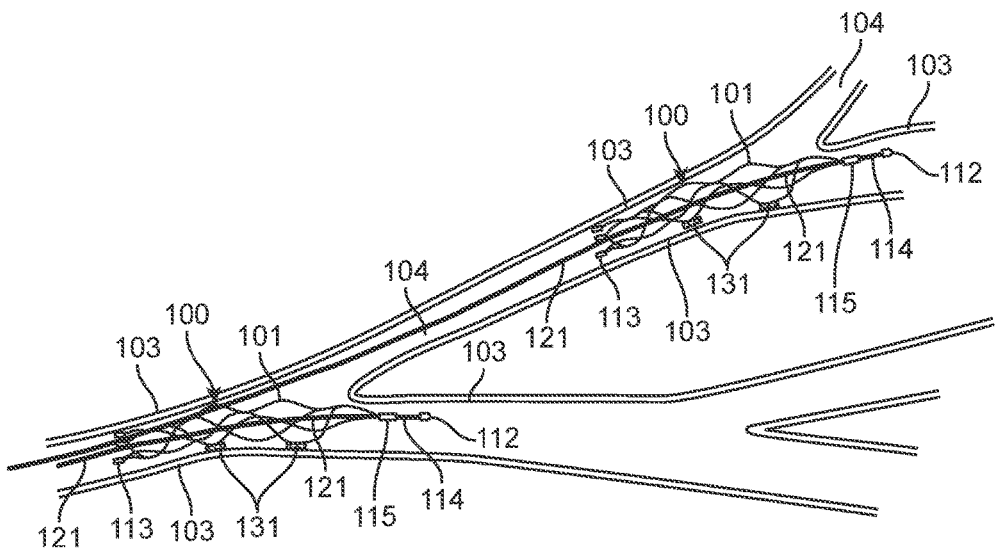
FIG. 29 is a diagrammatic illustration showing multiple vessels with multiple devices.

FIG. 29 shows a vessel with multiple devices 100 inserted in different vessels 104 to access different areas.

Figure 30:
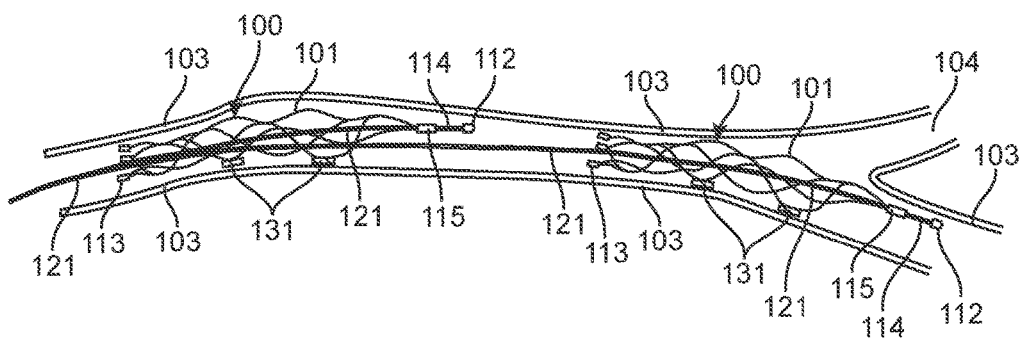
FIG. 30 is a diagrammatic illustration showing a single vessel with multiple devices.

FIG. 30 shows a single vessel 104 with multiple devices 100 implanted to cover a larger area.

Figure 31:
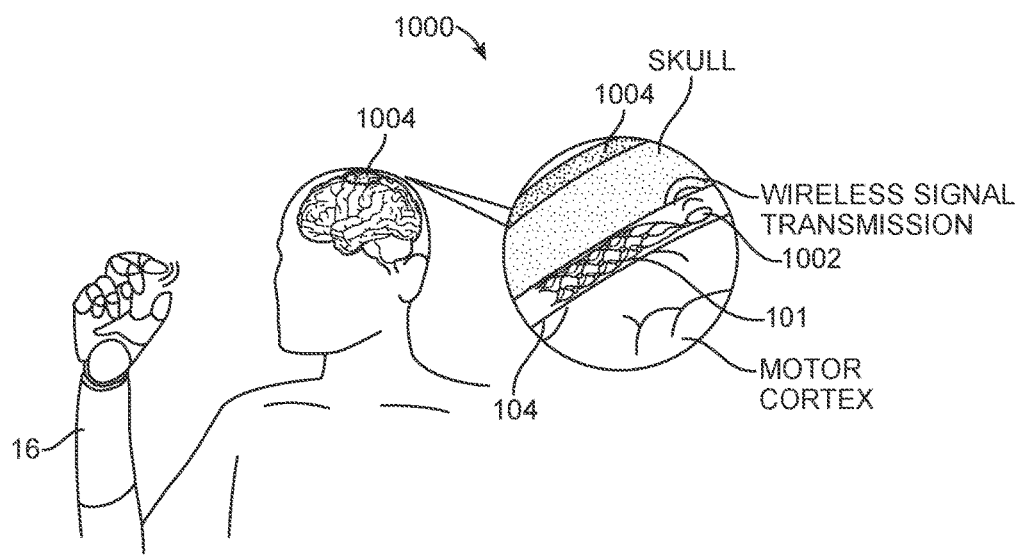
FIG. 31 is a diagrammatic illustration of a wireless electrode system.

FIG. 31 a wireless electrode system 1000 showing electrodes mounted on a stent 101 within a blood vessel 104 overlying the motor cortex in a human that are picking up neural information and relaying this information to a wireless transmitter 1002 located on the stent 101. Note the stent 101 has been deployed and the stylet has been removed (ie, only the stent 101, electrodes, electrode wires and wireless system 1002 remains). The information is wirelessly transmitted through the skull to a wireless received 1004 placed on the head, which in turn, decodes and transmits the acquired neural information to a prosthetic limb 16.

Figure 32:
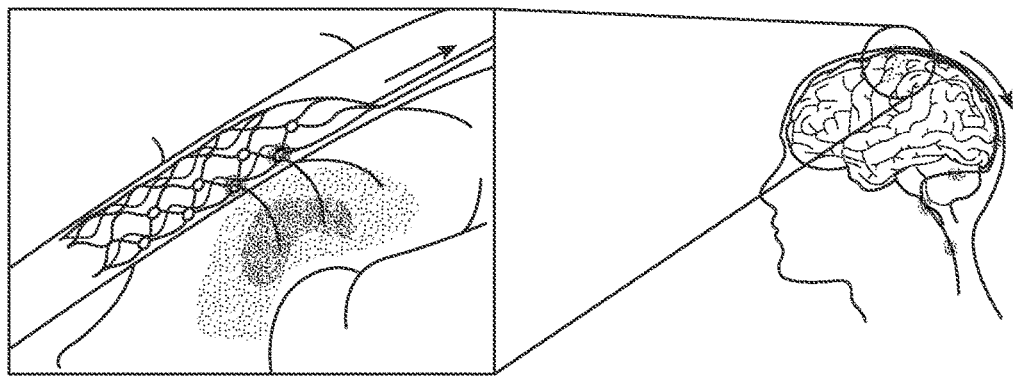
FIG. 32 is a diagrammatic illustration of the system being used to record neural information or stimulation of neurons from the superior sagittal sinus (SSS) or branching cortical veins of a patient using the device.

As shown in FIG. 32, the device 100 can be used to record neural information or stimulation of neurons from the superior sagittal sinus (SSS) or branching cortical veins of a patient using the device 100, including the steps of: (a) implanting the device in either the superior sagittal sinus or branching cortical veins; (b) receiving activity; and (c) generating data representing said activity; and (d) transmitting said data to a control unit. Stent 101 implanted in SSS over motor cortex acquiring (i.e. receives) signals that are fed through the wire to external equipment 12.

Figure 33:
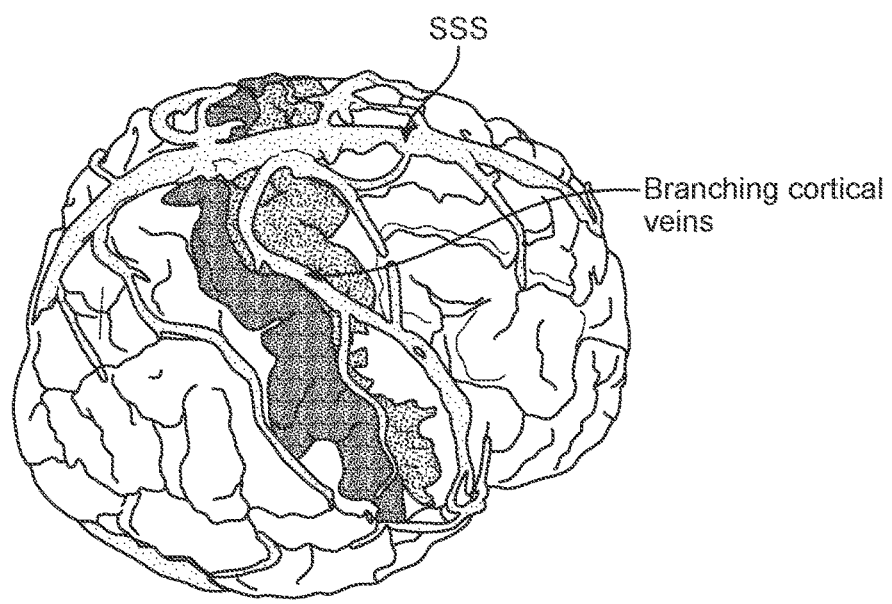
FIG. 33 shows an image reconstruction of a human brain (eyes facing left) demonstrating superior sagittal sinus and branching cortical veins near the motor cortex (red) and sensory cortex (yellow)

FIG. 33 shows an image reconstruction of a human brain (eyes facing left) demonstrating superior sagittal sinus and branching cortical veins near the motor cortex (red) and sensory cortex (yellow)

Figure 34:
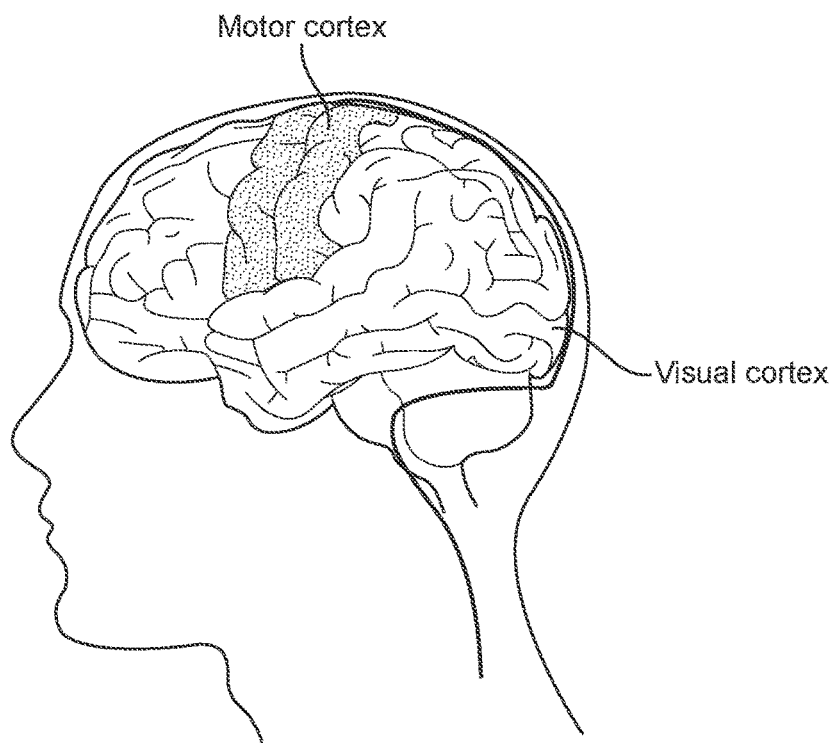
FIG. 34 is a diagrammatic illustration showing a method for stimulation and recording neural information or stimulation of neurons from the visual cortex of a patient using the device.

FIG. 34 shows a method of for stimulation and recording neural information or stimulation of neurons from the visual cortex of a patient using the device 100, including the steps of: (a) implanting the device in a vessel in the visual cortex of the patient; and (b) recording neural information associated with the vessel or stimulating neurons in accordance with received stimulation data.

Figure 35:
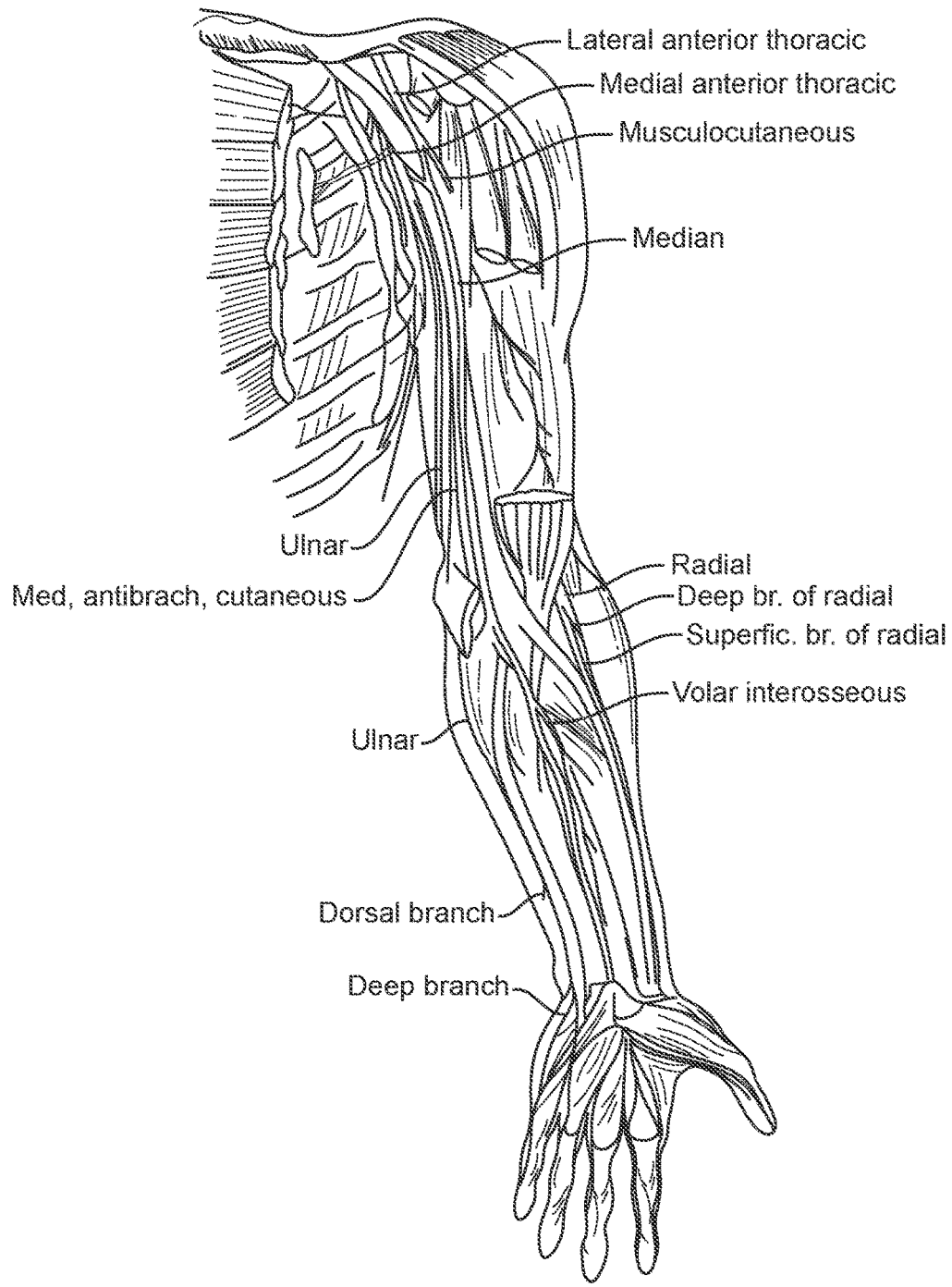
FIG. 35 is a diagrammatic illustration showing vessels and muscles in a human arm.

As particularly shown in FIG. 35, the device 100 is delivered through a vessel 104 deposited in a muscle for direct muscular stimulation or recording.

The device 100 can be delivered through a vessel adjacent to a peripheral nerve (such as shown in FIG. 35) for stimulation or recording.

Figure 36:
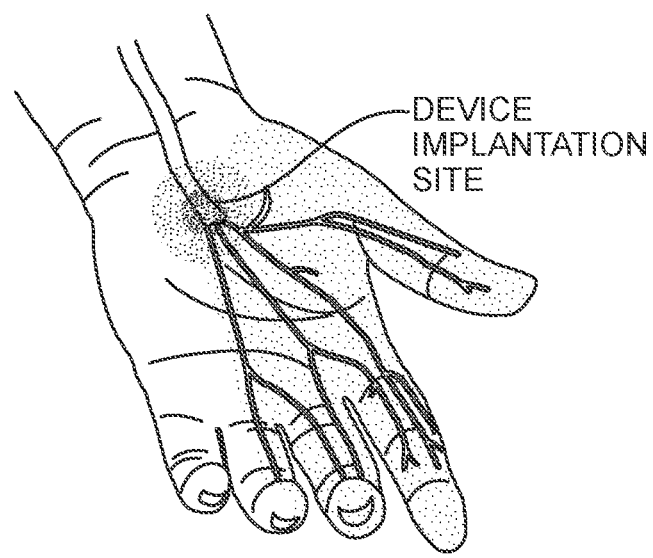
FIG. 36 is an illustration of a human hand showing possible implant location to enable neural stimulation or measurement.

The device is delivered through a vessel adjacent to a sympathetic or parasympathetic nerve for stimulation or ablation As shown in FIG. 36, one example of a peripheral nerve (the median nerve in this example) showing possible implant location to enable neural stimulation or measurement.

Figure 38A:
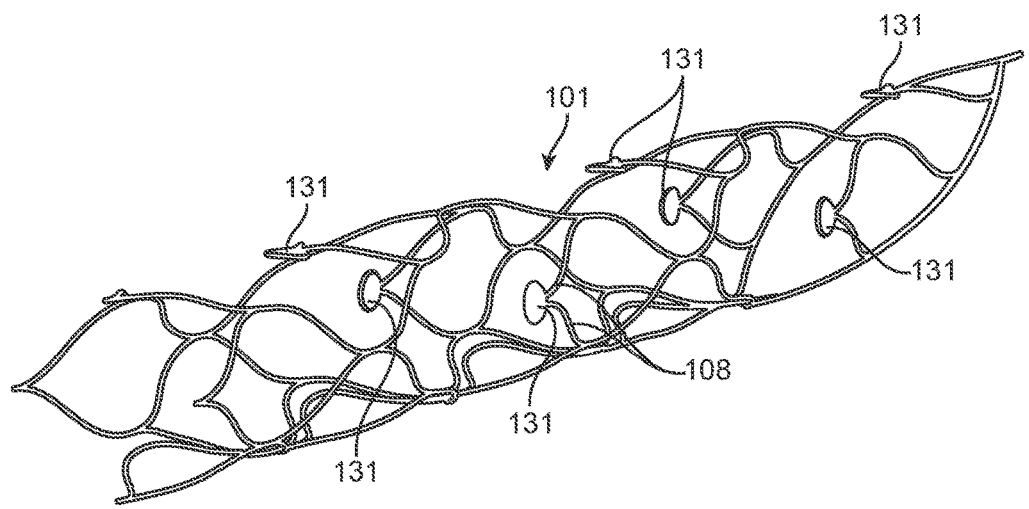
FIGS. 38A-38D illustrate examples of stents or scaffoldings having a plurality of electrodes disposed about the stent body.

FIG. 38A illustrates another example of a stent or scaffolding 101 having a plurality of electrodes 131 disposed about the stent 101 body. For purposes of illustration, the stent 101 is shown without any connecting structure that electrically couples the electrodes to leads or other such structure that allows electrical communication between the electrodes and control unit as described above. In the illustrated variation, the electrodes 131 are dispersed about the body of the stent 101 and are located at the joining or apex of joining struts 108. In such a configuration, where instead of having cells shaped like diamonds, the cells are shaped like a 'V'. This configuration can enhance the apposition between the electrodes 131 and the tissue or vessel wall.

FIG. 38A also illustrates a variation of a stent 101 that can be fabricated where stent structure comprises an integrated conductive layer that extends through a portion or more of the stent strut 108 and where the electrode 131 is formed through an exposed portion of the integrated conductive layer. Such a stent configuration, as described in detail below, permits a stent 101 electrode 131 assembly, which embeds electrodes and conductive electrode tracks into the stent lattice or strut itself. Such a construction reduces or eliminates the requirement to use fixation methods (i.e., adhesives, glues, fasteners, welds, etc.) to mount electrodes to the body of the stent. Such a construction further reduces or eliminates the need to further weld or electrically connect electrodes to wires. Another benefit is that conventional wire-connected-electrodes require accommodation of the wires about the stent struts and through the body of the stent.

Figure 38B:
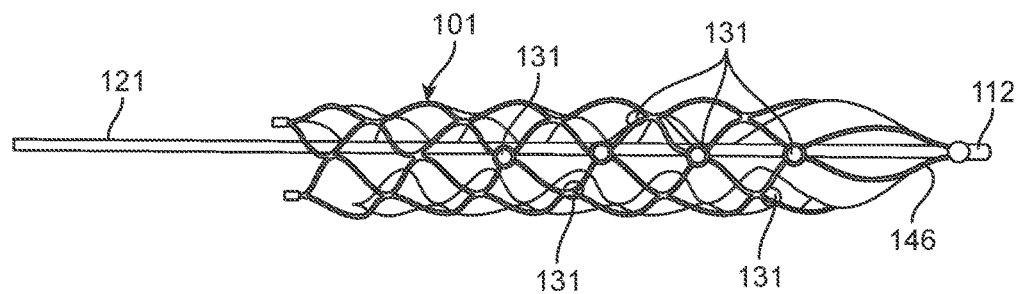
Figure 38C:
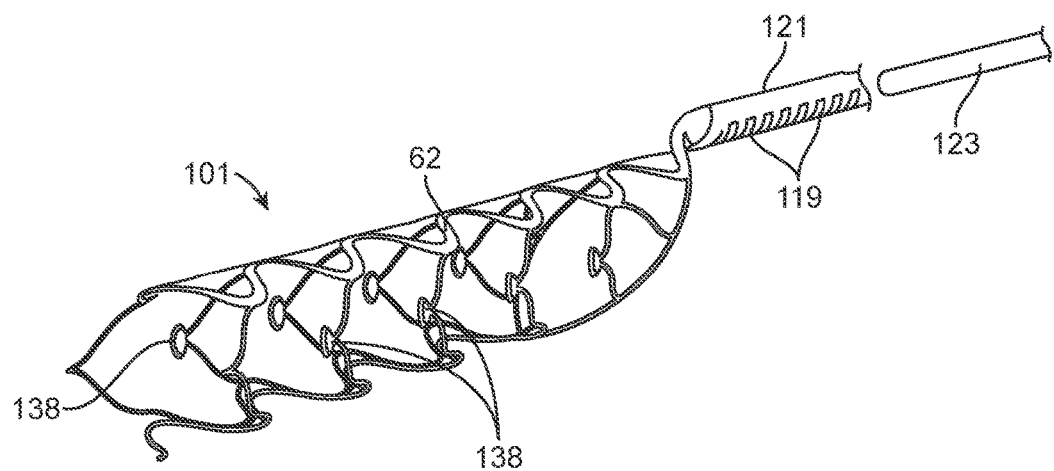
Figure 38D:
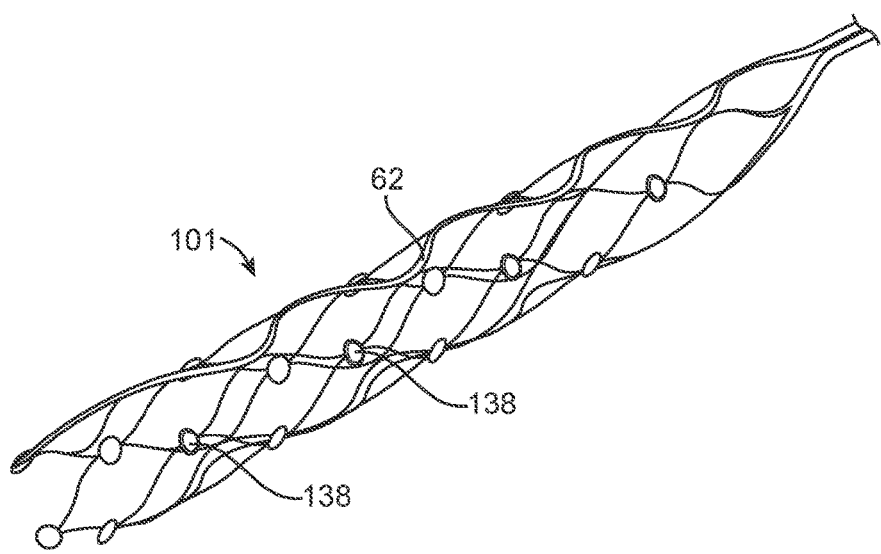

FIG. 38B illustrates a stent structure 101 with integrated electrodes 131, where the stent structure is coupled to a shaft 121 at a distal end 146. The shaft, as described herein, can electrically couple the electrodes 131 to one or more control units (not shown) as described herein. In one example, the shaft 121 can comprise a guidewire, push wire other tubular structure that contains wires or conductive members extending therein and are coupled to the conductive layer of the stent at the distal end 146. Alternatively, FIGS. 38C and 38D shows a variation of stents 101 that can be fabricated such that the shaft 121 is part of or integral with the stent structure, where the conductive layer extends through a portion or all of the stent to the shaft 121. Such a construction further eliminates the need for joining the shaft to the stent structure at the working end of the stent. Instead, the joining of the stent structure (forming the shaft) to a discrete shaft can be moved proximally along the device. Such a construction allows the working end of the stent and shaft to remain flexible. The stent structures shown in FIGS. 38C and 38D can also include an optional reinforced section 62 as discussed above. FIG. 38C further illustrates a hollow shaft 121, which allows insertion of a stylet 123 therethrough to assist in positioning of the device or permits coupling of wires or other conductive members therethrough. Furthermore, the shaft 121 can include any number of features 119 that improve flexibility or pushability of the shaft through the vasculature.

The electrical connection of the electrodes 131 to leads extending through the device can be accomplished by the construction of one or more connection pads (similar in construction to the electrodes described below) where the size of the pads ensures sufficient contact with the wire/lead, the type of pads ensures robustness and reduces track fatigue when crimped and attached. The section containing the pads can be compressed into a tube at, for example, distal section 146 to enable insertion of a cable 121.

In certain variations, the connection pads should be able to feed through the catheter. Furthermore, the connection pads 132 can include one or more holes or openings that enable visual confirmation that the pads are aligned with contacts on the lead. These holes/openings also enables direct/laser welding or adhesion of the contact leads (inside tube 121) and the contact pads (on the inside of the tube spanning through the hole to the outside)

In one example, a coaxial-octofilar cable (i.e. an inner cable with 8 wires positioned inside an outer cable having 8 wires) is used to enhance fatigue resistance and to ensure that wires can fit within constraints (i.e., can be inserted through a sufficiently small catheter, and can have an internal stylet as required).

Figure 39A:
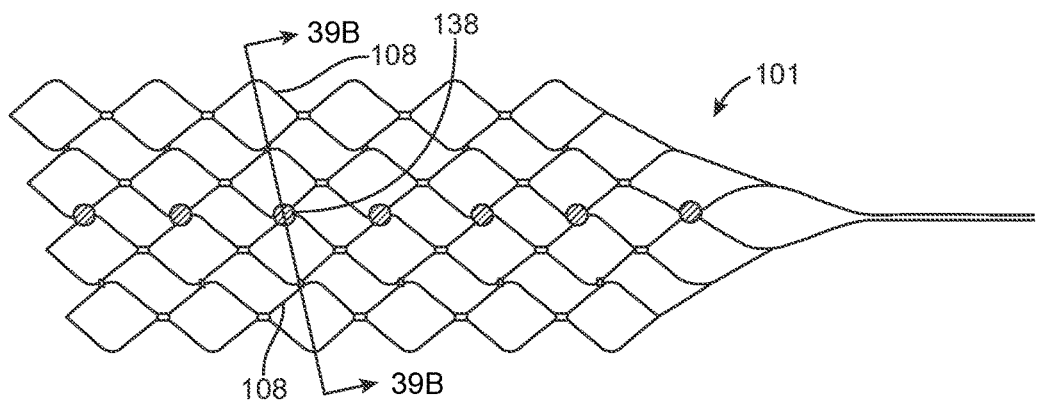
FIGS. 39A-39C illustrate an example of integrated or embedded electrodes.

FIGS. 39A-49C illustrate one example of a stent structure 101 constructed with an embedded electrode and conductive path. FIG. 39A illustrates an example of a stent structure 101 in a planar configuration with electrodes 138 in a linear arrangement for purposes of illustration only. Clearly, any configuration of electrodes is within the scope of this disclosure. Specifically, in those variations of stent structures useful for neurological applications, the stent structure can comprise a diameter that is traditionally greater than existing neurological stents. Such increased diameter can be useful due to the stent structure being permanently implanted and while requiring apposition of electrodes against the vessel/tissue wall. Moreover, in some variations, the length of such stent structures can include lengths up to and greater than 20 mm to accommodate desired placement along the human motor cortex. For example, variations of the device require a stent structure that is sufficiently long enough to cover the motor cortex and peripheral cortical areas. Such lengths are not typically required for existing interventional devices aimed at restoring flow or addressing aneurysms or other medical conditions. In addition, in certain variations, the electrical path between certain electrodes can be isolated. In such a case, the electrically conductive material 50 can be omitted from certain stent struts to form a pattern that allows an electrode to have an electrical conduction path to a contact pad or other conductive element but the electrical conduction path is electrically isolated from a second electrode having its own second electrically conductive path.

Placement of the electrodes in a specific pattern (e.g., a corkscrew configuration or a configuration of three linear (or corkscrew oriented) lines that are oriented 120 degrees from each other) can ensure a deployed electrode orientation that directs electrodes towards the brain. Once implanted, orientation is not possible surgically (i.e., the device will be implanted and will be difficult if not impossible to rotate). Therefore, variations of the device will be desirable to have an electrode pattern that will face towards the desired regions of the brain upon delivery.

Electrode sizing should be of a sufficient size to ensure high quality recordings and give large enough charge injection limits (the amount of current that can be passed through the electrodes during stimulation without damaging the electrodes which in turn may damage tissue). The size should also be sufficient to allow delivery via a catheter system.

Figure 39B:
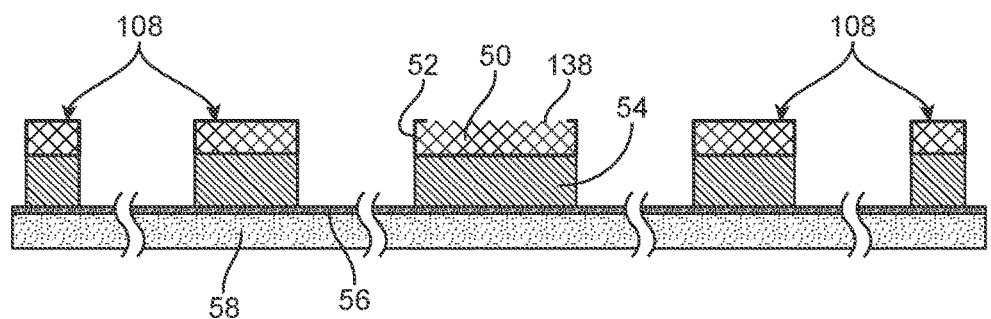
Figure 39C:
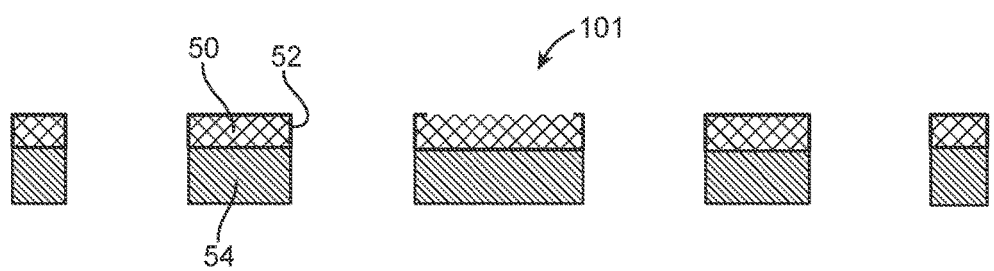

FIGS. 39B and 39C illustrates a cross-sectional view of the stent structure of FIG. 39A taken along line 39B-39B to further illustrate one variation of a manufacturing technique of using MEMS (microelectrical mechanical systems) technology to deposit and structure thin film devices to fabricate a stent structure with electrodes and a conductive path embedded into the stent lattice or struts. The spacing of the struts in FIGS. 39B and 39C are compressed for illustrative purposes only.

As discussed above, embedding the electrode and conductive path presents advantages in the mechanical performance of the device. Furthermore, embedding of electrodes provides the ability to increase the number of electrodes mounted on the structure give that the conductive paths (30-50×200-500 nm) can be smaller than traditional electrode wires (50-100 μm).

Manufacture of thin-film stents can be performed by depositing Nitinol or other superelastic and shape memory materials (or other materials for deposition of electrodes and contacts (including but not limited to gold, platinum, iridium oxide) through magnetron sputtering in a specific pattern (56) using a sacrificial layer (58) as a preliminary support structure. Removal of the support structure (54) enables the thin film to be further structured using UV-lithography and structures can be designed with thicknesses corresponding with radial force required to secure the electrodes against a vessel wall.

Electrical insulation of electrodes is achieved by RF sputtering and deposition of a non-conductive layer (52) (eg, SiO) onto the thin-film structure (54). Electrodes and electrode tracks (50) are sputter deposited onto the non-conductive layer (using conductive and biomedically acceptable materials including gold, Pt, Ti, NiTi, PtIr), with an additional non-conductive layer deposited over the conductive track for further electrical isolation and insulation. As shown, conducting path 50 is left exposed to form the electrode 138 (similarly, a contact pad area can remain exposed). Finally, the sacrificial layer 56 and substrate are removed leaving the stent structure 101 as shown in FIG. 39C.

In certain variations where the base structure 54 comprises superelastic and shape-memory materials (i.e. Nitinol), the stent structure 101 can be annealed in a high vacuum chamber to avoid oxidation during the annealing process. During heat treatment, the amorphous Nitinol structure 54 crystallizes to obtain superelasticity and can be simultaneously shape set into a cylindrical or other shape as desired. The structure 101 can then be heat treated.

Figure 40A:
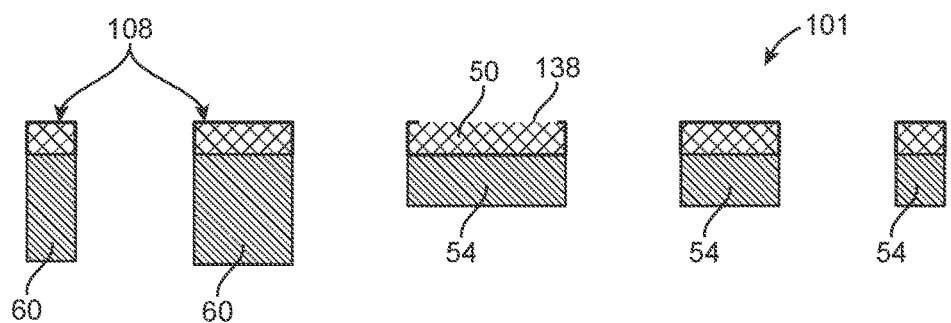
FIGS. 40A-40B show an example of a stent structure fabricated with dimensional variation to impart specific characteristics to the stent.

FIG. 40A, which is a partial sectional view of taken along lines 40A-40A of FIG. 41B, illustrate an additional variation of a stent structure 101 fabricated via MEMS technology where one or more stent struts 108 can be dimensionally altered to impart desired structural or other aspects to the stent structure 101. For example, in the illustrated variation, certain stent struts 108 are dimensionally altered such that the support material 60 comprises a greater thickness than adjacent stent structures 108. However, such dimensional variation is not limited to thickness but can also include width, shape, etc.

Figure 40B:
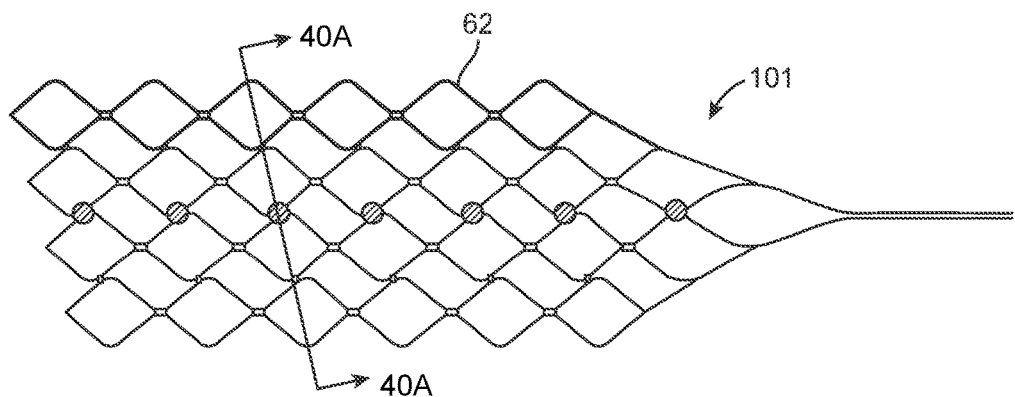

FIG. 40B illustrates the stent structure 101 resulting from the dimensionally altered struts resulting in a sinusoidal section 62 of the stent structure 101 that comprises a greater stiffness (resulting from the increased thickness). Such a configuration allowing the stent device to be pushed through a catheter rather than conventional requirements to be unsheathed (where the sheath is pulled back over the stent). Conventional stents are made from a thin lattice of Nitinol diamonds or cells. This sinusoidal section 62 can function like a backbone and gives forward pushing strength to the device without restricting super-elasticity and the ability for the stent to compress and expand. Clearly, any number of variations of dimensionally altered strut sections are within the scope of this disclosure.

Many modifications will be apparent to those skilled in the art without departing from the scope of the present invention.

The reference to any prior art in this specification is not, and should not be taken as, an acknowledgment or any form of suggestion that the prior art forms part of the common general knowledge in Australia In this specification and the claims that follow, unless stated otherwise, the word "comprise" and its variations, such as "comprises" and "comprising", imply the inclusion of a stated integer, step, or group of integers or steps, but not the exclusion of any other integer or step or group of integers or steps.

References in this specification to any prior publication, information derived from any said prior publication, or any known matter are not and should not be taken as an acknowledgement, admission or suggestion that said prior publication, or any information derived from this prior publication or known matter forms part of the common general knowledge in the field of endeavor to which the specification relates.

We claim:

1. A medical device for use within a tubular body having a lumen, the medical device comprising:
   a frame structure forming a plurality of struts, where the frame structure is moveable between a reduced profile and an expanded profile in which a diameter of the frame structure increases;
   where at least one of the plurality of struts forming the frame structure comprises an electrically conductive material on a support material, the electrically conductive material extending along at least a portion of the strut and being covered with a non-conductive material;
   at least one electrode formed by an opening in the non-conductive material on the portion of the strut, where the at least one electrode is located at a cross link between joining struts such that an integrity of the at least one electrode is not affected during movement of the frame structure between the reduced profile and the expanded profile; and
   a lead located at an end of the frame structure and extends away from the frame structure, where the electrically conductive portion extends along the strut to electrically connect with the lead.

2. The medical device of claim 1, further comprising a connector block configured to electrically couple the medical device to an external device, where the lead extends from the frame structure to the connector block.

3. The medical device of claim 1, where the at least one electrode comprises a greater surface area than an adjacent region of the strut.

4. The medical device of claim 1, where the at least one electrode comprises a plurality of electrodes.

5. The medical device of claim 4, where the plurality of electrodes are aligned in a linear pattern on the frame structure selected from the group consisting of a linear pattern, a sinusoidal pattern, and a circumferential pattern.

6. The medical device of claim 4, where the plurality of electrodes are located at each cross-link of each connecting strut.

7. The medical device of claim 1, further comprising at least one reinforced strut having a support material having a width or thickness greater than at least a second strut.

8. The medical device of claim 7, where the reinforced strut extends along a length of the frame structure.

9. The medical device of claim 1, where the at least one strut comprises a first strut and further comprising a second strut forming the frame structure, where the second strut comprises an electrically conductive material on a support material, the electrically conductive material extending along at least a portion of the second strut and being covered with a non-conductive material, where the electrically conductive material of the first strut is electrically isolated from the electrically conductive material of the second strut and where the electrically conductive material of the second strut extends along the strut to electrically connect with the lead; and
   at least a second electrode formed by an opening in the non-conductive material on the portion of the second strut.

10. The medical device of claim 1, where the frame structure is tubular shaped or c-shaped.

11. The device of claim 1, including a non-traumatic buffer coupled to a leading end of the device for reducing risk of vascular puncture during implantation.

12. The device of claim 1, further comprising an electronics assembly directly mounted to the frame structure.

13. The device of claim 12, where the electronics assembly includes:
   (a) circuitry for stimulating neural tissue, including one or more of the following:
      (i) current and/or voltage sources;
      (ii) batteries and/or capacitors or charge/energy storing components; and
      (iii) switch matrices, and/or
   (b) circuitry for recording neural activity including one or more of:
      (i) amplifiers;
      ii) power sources; and
      (iii) switch matrices.

14. The medical device of claim 1, wherein the cross link between adjoining struts terminates in an apex, where the electrode is located on the apex to enhance apposition between the electrode and the tubular body.

15. The medical device of claim 1, further comprising:
   a control unit adapted for communication with the medical device of claim 1, wherein the control unit is adapted to:
   (i) receive data from the device representing activity of media proximal to the device;
   (ii) generate a control signal; and
   (iii) transmit the control signal to said apparatus.

16. The system of claim 15, where the medical device comprises:
- a stent movable between a collapsed condition of use for insertion into said vessel and an expanded condition of use for resiliently bearing against a wall of said vessel;
- one or more electrodes on the stent and configured for stimulating and/or sensing activity of media proximal to the device, wherein the media includes tissue and/or fluid.

17. The system of claim 15, where the control unit is adapted to be inset under the skin of the animal.

18. The system of claim 15, where the apparatus includes one or more of the following:
- an exoskeleton;
- a prosthetic limb;
- a wheelchair;
- a computer; and/or
- an electrical or electro-mechanical device.

19. The system of claim 15, further comprising a communication conduit that transmits data between the device and the control unit.

20. The system of claim 15, wherein the control unit is further adapted to generate a device control signal and transmit the device controls signal to the device such that the device can stimulate the media.

21. The system of claim 15, where the control unit includes a housing formed in at least two parts.

22. The system of claim 21, where the at least two parts of the housing are
- magnetically secured;
- aligned using pins; and
- include a gasket to prevent water ingress.

23. A medical device for use within a tubular body having a lumen, the medical device comprising:
- a frame structure forming a plurality of struts, where the frame structure is moveable between a reduce profile and an expanded profile in which a diameter of the frame structure increases;
- where at least one of the plurality of struts forming the frame structure comprises an electrically conductive material on a support material, the electrically conductive material extending along at least a portion of the strut and being covered with a non-conductive material, where the plurality of struts includes a plurality of pairs of struts where each pair forms a v-shaped apex unattached to adjacent struts;
- at least one electrode formed by an opening in the non-conductive material on the v-shaped apex portion of the strut, to enhance opposition between the at least one electrode and a wall of the tubular body; and
- a lead located at an end of the frame structure and configured to be in electrical communication with the electrically conductive portion, the lead extending from the frame structure.

24. The medical device of claim 23, wherein the lead is coupled to a distal end of the frame structure and extends through a proximal end of the frame structure to the distal end of the frame structure.

* * * * *